(12) United States Patent
Buchbinder et al.

(10) Patent No.: US 10,779,945 B2
(45) Date of Patent: Sep. 22, 2020

(54) PERCUTANEOUS TRANSCATHETER REPAIR OF HEART VALVES VIA TRANS-APICAL ACCESS

(71) Applicant: VALCARE, INC., Newport Beach, CA (US)

(72) Inventors: Maurice Buchbinder, La Jolla, CA (US); Samuel M. Shaolian, Newport Beach, CA (US)

(73) Assignee: VALCARE, INC., Newport Beach, CA (US)

( * ) Notice: Subject to any disclaimer, the term of this patent is extended or adjusted under 35 U.S.C. 154(b) by 0 days.

(21) Appl. No.: 15/195,433

(22) Filed: Jun. 28, 2016

(65) Prior Publication Data

US 2016/0331534 A1 Nov. 17, 2016

Related U.S. Application Data

(62) Division of application No. 13/397,545, filed on Feb. 15, 2012, now Pat. No. 9,402,721.
(Continued)

(51) Int. Cl.
*A61F 2/24* (2006.01)
*A61B 17/04* (2006.01)
(Continued)

(52) U.S. Cl.
CPC ........ *A61F 2/2466* (2013.01); *A61B 17/0469* (2013.01); *A61F 2/2448* (2013.01);
(Continued)

(58) Field of Classification Search
CPC ................ A61F 2/2466; A61F 2/2433; A61M 2025/1061; A61M 2025/1072; A61M 2025/1047
See application file for complete search history.

(56) References Cited

U.S. PATENT DOCUMENTS

| 4,602,911 A | 7/1986 | Ahmadi et al. |
| 5,236,440 A | 8/1993 | Hlavacek |

(Continued)

FOREIGN PATENT DOCUMENTS

| DE | 102014102653 A1 | 9/2015 |
| EP | 2600799 A | 6/2013 |

(Continued)

OTHER PUBLICATIONS

International Search Report and Written Opinion for PCT/US2011/046659 dated Jun. 4, 2012.
(Continued)

*Primary Examiner* — Rebecca S Preston
(74) *Attorney, Agent, or Firm* — Pepper Hamilton LLP

(57) ABSTRACT

Apparatus, systems, and methods are provided for repairing heart valves through percutaneous transcatheter delivery and fixation of annuloplasty rings to heart valves via a trans-apical approach to accessing the heart. A guiding sheath may be introduced into a ventricle of the heart through an access site at an apex of the heart. A distal end of the guiding sheath can be positioned retrograde through the target valve. An annuloplasty ring arranged in a compressed delivery geometry is advanced through the guiding sheath and into a distal portion of the guiding sheath positioned within the atrium of the heart. The distal end of the guiding sheath is retracted, thereby exposing the annuloplasty ring. The annuloplasty ring may be expanded from the delivery geometry to an operable geometry. Anchors on the annuloplasty ring may be deployed to press into and engage tissue of the annulus of the target valve.

8 Claims, 31 Drawing Sheets

Related U.S. Application Data

(60) Provisional application No. 61/492,279, filed on Jun. 1, 2011.

(51) Int. Cl.

| | | |
|---|---|---|
| *A61M 25/10* | (2013.01) | |
| *A61F 2/962* | (2013.01) | |
| *A61F 2/95* | (2013.01) | |
| *A61F 2/958* | (2013.01) | |
| *A61B 17/88* | (2006.01) | |
| *A61B 18/00* | (2006.01) | |

(52) U.S. Cl.
CPC ...... *A61M 25/1011* (2013.01); *A61B 17/8855* (2013.01); *A61B 2017/0474* (2013.01); *A61B 2018/0025* (2013.01); *A61F 2/2433* (2013.01); *A61F 2/2442* (2013.01); *A61F 2/2445* (2013.01); *A61F 2/95* (2013.01); *A61F 2/958* (2013.01); *A61F 2/962* (2013.01); *A61F 2210/0014* (2013.01); *A61F 2210/0023* (2013.01); *A61F 2210/0033* (2013.01); *A61F 2210/0066* (2013.01); *A61F 2220/0016* (2013.01); *A61F 2220/0025* (2013.01); *A61F 2220/0075* (2013.01); *A61F 2230/0006* (2013.01); *A61F 2230/0008* (2013.01); *A61F 2250/001* (2013.01); *A61M 2025/1047* (2013.01); *A61M 2025/1061* (2013.01); *A61M 2025/1072* (2013.01)

(56) References Cited

U.S. PATENT DOCUMENTS

| | | | |
|---|---|---|---|
| 5,306,296 A | | 4/1994 | Wright et al. |
| 5,695,518 A | | 12/1997 | Laerum |
| 5,716,370 A | | 2/1998 | Williamson, IV et al. |
| 5,855,614 A | | 1/1999 | Stevens et al. |
| 6,113,611 A | | 9/2000 | Allen et al. |
| 6,231,602 B1 | | 5/2001 | Carpentier et al. |
| 6,619,291 B2 | | 9/2003 | Hlavka et al. |
| 6,629,534 B1 | | 10/2003 | St. Goar et al. |
| 6,669,687 B1 | | 12/2003 | Saadat |
| 6,689,048 B2 | | 2/2004 | Vanden Hoek et al. |
| 6,726,704 B1 | | 4/2004 | Loshakove et al. |
| 6,776,784 B2 | | 8/2004 | Ginn |
| 6,790,229 B1 | * | 9/2004 | Berreklouw ............ A61B 17/11 |
| | | | 606/153 |
| 6,797,002 B2 | | 9/2004 | Spence et al. |
| 6,805,711 B2 | | 10/2004 | Quijano et al. |
| 6,893,459 B1 | | 5/2005 | Macoviak |
| 7,101,395 B2 | | 9/2006 | Tremulis et al. |
| 7,114,953 B1 | | 10/2006 | Wagner |
| 7,175,660 B2 | | 2/2007 | Cartledge et al. |
| 7,238,191 B2 | | 7/2007 | Bachmann |
| 7,285,087 B2 | | 10/2007 | Moaddeb et al. |
| 7,297,150 B2 | | 11/2007 | Cartledge et al. |
| 7,569,072 B2 | | 8/2009 | Berg et al. |
| 7,594,887 B2 | | 9/2009 | Moaddeb et al. |
| 7,635,329 B2 | | 12/2009 | Goldfarb et al. |
| 7,655,040 B2 | | 2/2010 | Douk et al. |
| 7,717,954 B2 | | 5/2010 | Solem et al. |
| 7,722,668 B2 | | 5/2010 | Moaddeb et al. |
| 7,758,637 B2 | | 7/2010 | Starksen et al. |
| 7,837,729 B2 | | 11/2010 | Gordon et al. |
| 7,988,725 B2 | | 8/2011 | Gross et al. |
| 8,163,014 B2 | | 4/2012 | Lane et al. |
| 8,182,529 B2 | | 5/2012 | Gordon et al. |
| 8,236,049 B2 | | 8/2012 | Rowe et al. |
| 8,287,591 B2 | | 10/2012 | Keidar et al. |
| 8,518,107 B2 | | 8/2013 | Tsukashima et al. |
| 8,579,968 B1 | | 11/2013 | Shannon et al. |
| 2002/0151961 A1 | | 10/2002 | Lashinski et al. |
| 2002/0151970 A1 | | 10/2002 | Garrison et al. |
| 2002/0188170 A1 | | 12/2002 | Santamore et al. |
| 2002/0198526 A1 | | 12/2002 | Shaolian et al. |
| 2003/0050693 A1 | | 3/2003 | Quijano et al. |
| 2003/0078465 A1 | | 4/2003 | Pai et al. |
| 2003/0078671 A1 | | 4/2003 | Lesniak et al. |
| 2003/0191528 A1 | | 10/2003 | Quijano et al. |
| 2003/0198605 A1 | | 10/2003 | Montgomery |
| 2003/0199974 A1 | | 10/2003 | Lee et al. |
| 2004/0044364 A1 | | 3/2004 | DeVries et al. |
| 2004/0068276 A1 | | 4/2004 | Golden et al. |
| 2004/0122514 A1 | | 6/2004 | Fogarty et al. |
| 2004/0138744 A1 | | 7/2004 | Lashinski et al. |
| 2004/0148021 A1 | | 7/2004 | Cartledge et al. |
| 2004/0193191 A1 | | 9/2004 | Starksen et al. |
| 2004/0243230 A1 | * | 12/2004 | Navia .................. A61F 2/2445 |
| | | | 623/2.36 |
| 2004/0249391 A1 | | 12/2004 | Cummins |
| 2004/0260393 A1 | | 12/2004 | Randert et al. |
| 2004/0260394 A1 | | 12/2004 | Douk et al. |
| 2005/0020696 A1 | | 1/2005 | Montgomery et al. |
| 2005/0033325 A1 | | 2/2005 | May et al. |
| 2005/0065550 A1 | | 3/2005 | Starksen et al. |
| 2005/0090846 A1 | * | 4/2005 | Pederson et al. ...... A61M 29/00 |
| | | | 606/159 |
| 2005/0096740 A1 | | 5/2005 | Langberg et al. |
| 2005/0113910 A1 | | 5/2005 | Paniagua et al. |
| 2005/0137695 A1 | | 6/2005 | Salahieh et al. |
| 2005/0203549 A1 | | 9/2005 | Realyvasquez |
| 2005/0222678 A1 | | 10/2005 | Lashinski et al. |
| 2005/0240200 A1 | | 10/2005 | Bergheim |
| 2005/0267572 A1 | | 12/2005 | Schoon et al. |
| 2005/0283190 A1 | | 12/2005 | Huitema et al. |
| 2005/0288778 A1 | | 12/2005 | Shaoulian et al. |
| 2005/0288781 A1 | | 12/2005 | Moaddeb et al. |
| 2006/0009737 A1 | | 1/2006 | Whiting et al. |
| 2006/0129025 A1 | | 6/2006 | Levine et al. |
| 2006/0155165 A1 | | 7/2006 | Vanden Hoek et al. |
| 2006/0161169 A1 | | 7/2006 | Nieminen et al. |
| 2006/0184240 A1 | | 8/2006 | Jimenez et al. |
| 2006/0184242 A1 | | 8/2006 | Lichtenstein |
| 2006/0195134 A1 | | 8/2006 | Crittenden |
| 2006/0195183 A1 | * | 8/2006 | Navia .................. A61F 2/2409 |
| | | | 623/2.18 |
| 2006/0241748 A1 | | 10/2006 | Lee et al. |
| 2006/0282161 A1 | | 12/2006 | Huynh et al. |
| 2007/0016287 A1 | | 1/2007 | Cartledge et al. |
| 2007/0027533 A1 | | 2/2007 | Douk |
| 2007/0038296 A1 | | 2/2007 | Navia |
| 2007/0051377 A1 | | 3/2007 | Douk et al. |
| 2007/0067027 A1 | | 3/2007 | Moaddeb et al. |
| 2007/0073098 A1 | | 3/2007 | Lenker et al. |
| 2007/0080188 A1 | | 4/2007 | Spence et al. |
| 2007/0093854 A1 | | 4/2007 | Kayan |
| 2007/0118215 A1 | | 5/2007 | Moaddeb |
| 2007/0128132 A1 | | 6/2007 | Piergallini et al. |
| 2007/0135913 A1 | | 6/2007 | Moaddeb et al. |
| 2007/0142907 A1 | | 6/2007 | Moaddeb et al. |
| 2007/0213812 A1 | | 9/2007 | Webler et al. |
| 2007/0233239 A1 | | 10/2007 | Navia et al. |
| 2007/0239272 A1 | | 10/2007 | Navia et al. |
| 2007/0244553 A1 | | 10/2007 | Rafiee et al. |
| 2007/0244554 A1 | | 10/2007 | Rafiee et al. |
| 2007/0244555 A1 | * | 10/2007 | Rafiee .................. A61F 2/2445 |
| | | | 623/2.11 |
| 2007/0244556 A1 | | 10/2007 | Rafiee et al. |
| 2007/0250161 A1 | | 10/2007 | Dolan |
| 2007/0293942 A1 | * | 12/2007 | Mirzaee ................ A61F 2/2418 |
| | | | 623/2.11 |
| 2008/0177380 A1 | | 7/2008 | Starksen et al. |
| 2008/0177381 A1 | | 7/2008 | Navia et al. |
| 2008/0243220 A1 | | 10/2008 | Barker |
| 2008/0262513 A1 | | 10/2008 | Stahler et al. |
| 2008/0262609 A1 | | 10/2008 | Gross et al. |
| 2008/0306586 A1 | | 12/2008 | Cartledge et al. |
| 2009/0088838 A1 | | 4/2009 | Shaolian et al. |
| 2009/0118747 A1 | | 5/2009 | Bettuchi et al. |
| 2009/0149872 A1 | | 6/2009 | Gross et al. |
| 2009/0216322 A1 | | 8/2009 | Le et al. |
| 2009/0238778 A1 | | 9/2009 | Mordas et al. |

(56) References Cited

U.S. PATENT DOCUMENTS

| | | |
|---|---|---|
| 2009/0299470 A1 | 12/2009 | Rao et al. |
| 2010/0010616 A1 | 1/2010 | Drews et al. |
| 2010/0030014 A1 | 2/2010 | Ferrazzi |
| 2010/0063586 A1 | 3/2010 | Hasenkam et al. |
| 2010/0121433 A1 | 5/2010 | Bolling et al. |
| 2010/0161047 A1 | 6/2010 | Cabiri |
| 2010/0185274 A1 | 7/2010 | Moaddeb et al. |
| 2010/0211166 A1 | 8/2010 | Miller et al. |
| 2010/0249920 A1 | 9/2010 | Bolling et al. |
| 2010/0266989 A1 | 10/2010 | Piergallilni et al. |
| 2010/0280605 A1 | 11/2010 | Hammer et al. |
| 2010/0286767 A1 | 11/2010 | Zipory et al. |
| 2011/0022168 A1 | 1/2011 | Cartledge |
| 2011/0027753 A1 | 2/2011 | Maurat et al. |
| 2011/0034953 A1 | 2/2011 | Milo |
| 2011/0066231 A1 | 3/2011 | Cartledge et al. |
| 2011/0093062 A1 | 4/2011 | Cartledge et al. |
| 2011/0106245 A1 | 5/2011 | Miller et al. |
| 2011/0106247 A1 | 5/2011 | Miller et al. |
| 2011/0137397 A1 | 6/2011 | Chau et al. |
| 2011/0166649 A1 | 7/2011 | Gross et al. |
| 2011/0190879 A1 | 8/2011 | Bobo et al. |
| 2011/0208298 A1 | 8/2011 | Tuval et al. |
| 2011/0224785 A1 | 9/2011 | Hacohen |
| 2011/0257728 A1 | 10/2011 | Kuehn |
| 2011/0282361 A1 | 11/2011 | Miller et al. |
| 2011/0301698 A1 | 12/2011 | Miller et al. |
| 2011/0301699 A1 | 12/2011 | Saadat |
| 2012/0022557 A1 | 1/2012 | Cabiri et al. |
| 2012/0022644 A1 | 1/2012 | Reich et al. |
| 2012/0059458 A1 | 3/2012 | Buchbinder et al. |
| 2012/0095455 A1 | 4/2012 | Rodmond et al. |
| 2012/0123531 A1 | 5/2012 | Tsukashima et al. |
| 2012/0136436 A1 | 5/2012 | Cabiri et al. |
| 2012/0165930 A1 | 6/2012 | Gifford, III et al. |
| 2012/0245604 A1 | 9/2012 | Tegzes |
| 2012/0310330 A1 | 12/2012 | Buchbinder et al. |
| 2013/0087598 A1 | 4/2013 | Surti |
| 2013/0116780 A1 | 5/2013 | Miller et al. |
| 2013/0204361 A1 | 8/2013 | Adams et al. |
| 2013/0226289 A1 | 8/2013 | Shaolian et al. |
| 2013/0226290 A1 | 8/2013 | Yellin et al. |
| 2013/0282114 A1 | 10/2013 | Schweich, Jr. et al. |
| 2013/0289718 A1 | 10/2013 | Tsukashima et al. |
| 2013/0289720 A1 | 10/2013 | Dobrilovic |
| 2013/0304197 A1 | 11/2013 | Buchbinder et al. |
| 2014/0005778 A1 | 1/2014 | Buchbinder et al. |
| 2014/0046433 A1 | 2/2014 | Kovalsky |
| 2014/0058505 A1 | 2/2014 | Bielefeld |
| 2014/0114407 A1 | 4/2014 | Rajamannan |
| 2015/0173897 A1 | 6/2015 | Raanani et al. |
| 2015/0173987 A1 | 6/2015 | Albinmousa et al. |
| 2015/0351903 A1 | 12/2015 | Morriss et al. |
| 2016/0022419 A1 | 1/2016 | Yellin et al. |
| 2016/0038286 A1 | 2/2016 | Yellin et al. |
| 2016/0089235 A1 | 3/2016 | Yellin |
| 2016/0106420 A1 | 4/2016 | Foerster et al. |
| 2016/0120642 A1 | 5/2016 | Shaolian et al. |
| 2016/0120645 A1 | 5/2016 | Alon |
| 2017/0042670 A1 | 2/2017 | Shaolian et al. |
| 2017/0231763 A1 | 8/2017 | Yellin |
| 2018/0042723 A1 | 2/2018 | Yellin et al. |

FOREIGN PATENT DOCUMENTS

| | | | |
|---|---|---|---|
| KR | 10-2004-0095482 A | | 11/2004 |
| RU | 125062 U1 | | 2/2013 |
| WO | WO 1990/009153 A1 | | 2/1990 |
| WO | WO 2003/017874 A1 | | 3/2003 |
| WO | WO 2003/047467 A1 | | 6/2003 |
| WO | WO 2005/046488 | | 5/2005 |
| WO | WO 2005/046488 A2 | | 5/2005 |
| WO | WO 2009/052427 A1 | | 4/2009 |
| WO | WO 2009/120764 A2 | | 10/2009 |
| WO | WO 2010/004546 A1 | | 1/2010 |
| WO | WO 2010/085659 A1 | | 7/2010 |
| WO | WO 2011/011443 A2 | | 1/2011 |
| WO | WO 2011/097355 A2 | | 8/2011 |
| WO | WO 2012/004679 A2 | | 1/2012 |
| WO | WO 2012/019052 A2 | | 2/2012 |
| WO | WO 2012/063228 A1 | | 5/2012 |
| WO | WO 2012/095159 A2 | | 7/2012 |
| WO | WO 2012/106354 A1 | | 8/2012 |
| WO | WO 2012/167095 A2 | | 12/2012 |
| WO | WO 2013/095816 A1 | | 6/2013 |
| WO | WO 2013/128436 A1 | | 9/2013 |
| WO | WO 2013/130641 A1 | | 9/2013 |
| WO | WO 2013/175468 A2 | | 11/2013 |
| WO | WO 2014/145399 A1 | | 9/2014 |
| WO | WO 2014/189509 A1 | | 11/2014 |
| WO | WO 2014/190329 A1 | | 11/2014 |
| WO | WO 2014/210600 A2 | | 12/2014 |
| WO | 2015132668 A1 | | 9/2015 |

OTHER PUBLICATIONS

International Search Report and Written Opinion for PCT/US2012/040481 dated Dec. 6, 2012.
International Search Report and Written Opinion for PCT/US2013/073552 dated Mar. 6, 2014.
International Search Report and Written Opinion for PCT/US2014/030163 dated Aug. 27, 2014.
International Search Report and Written Opinion for PCT/US2014/039545 dated Oct. 22, 2014.
International Search Report for PCT/US2013/028065 dated Jun. 27, 2013.
International Search Report for PCT/US2013/058102 dated Apr. 21, 2014.
International Search Report and Written Opinion for PCT/US2013/042275 dated Feb. 20, 2014.
International Search Report for PCT/US2014/044920 dated Dec. 24, 2014.
Lendlein et al. "Biodegradable, Elastic Shape-Memory Polymers for Potential Biomedical Applications" May 31, 2002, Science 296:1673-1676.
Supplemental European Search Report and Written Opinion for EP 12793292.9 dated Dec. 1, 2014.
Supplementary Partial European Search Report for EP 13 75 5441 dated Nov. 3, 2015.
European Search Report in EP 17155803.4 dated Aug. 9, 2017.
Supplemental European Search Report and Written Opinion for EP 14762806.9 dated Jul. 29, 2016.
International Search Report and Written Opinion for PCT/US2017/046933 dated Dec. 21, 2017.
International Search Report and Written Opinion for PCT/US2018/022910 dated May 23, 2018.
Communication pursuant to Article 94(3) EPC for EP 14801009.3 dated Sep. 27, 2018.
International Search Report and Written Opinion for PCT2019/064289 dated Feb. 5, 2020.

\* cited by examiner

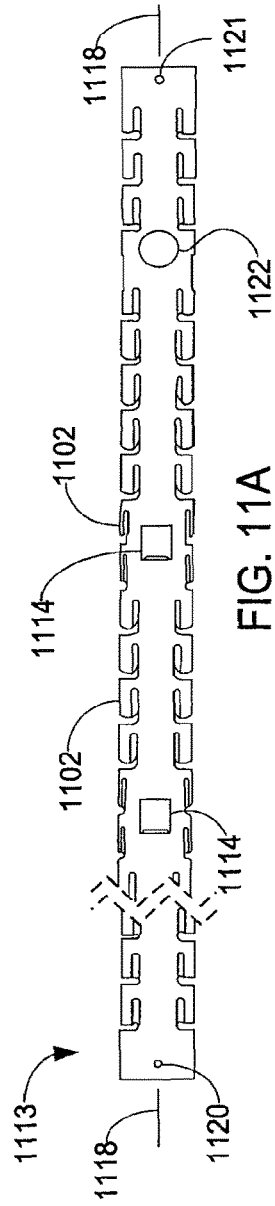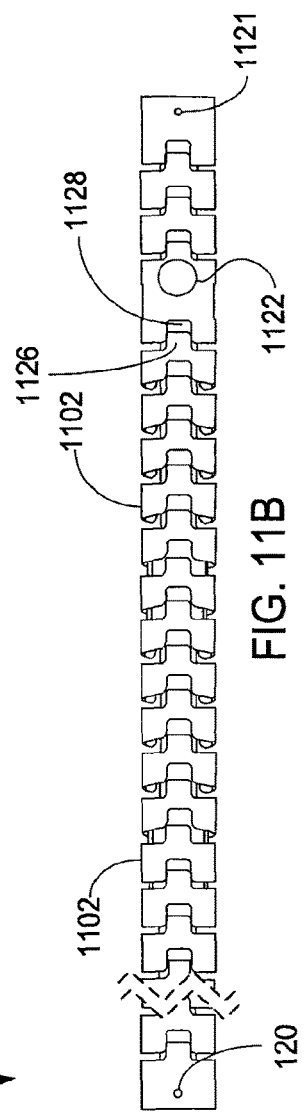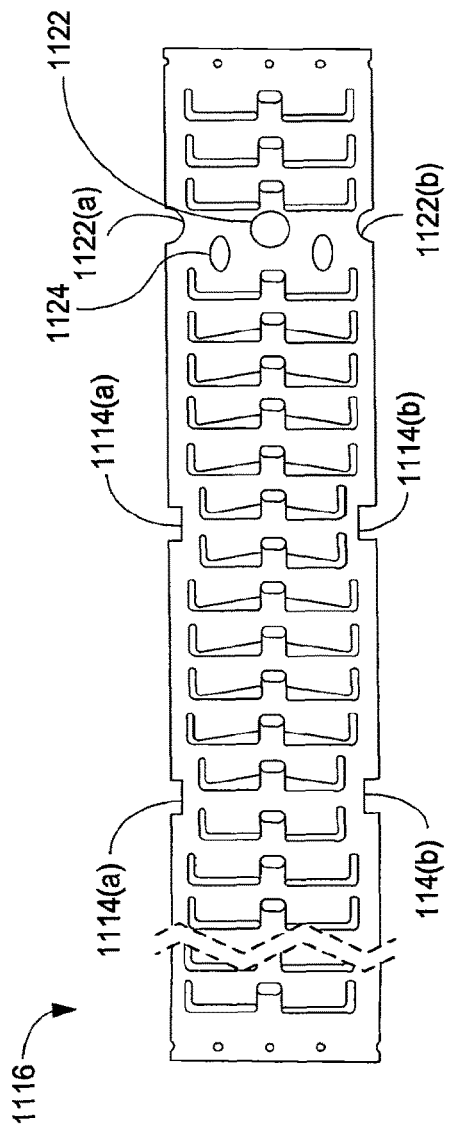

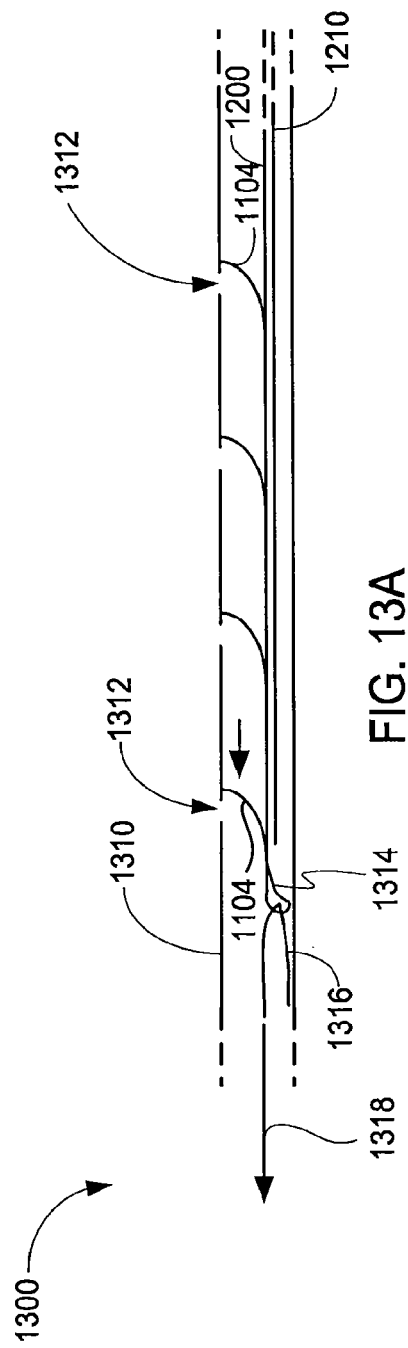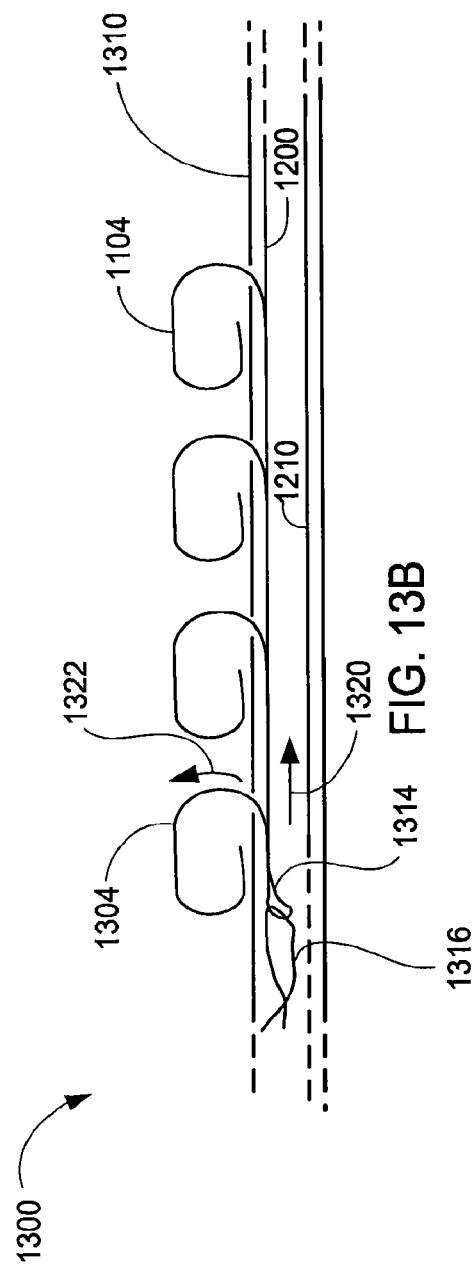
FIG. 13A
FIG. 13B

Circuitry in Ring

RF Power Source Circuitry

PERCUTANEOUS TRANSCATHETER REPAIR OF HEART VALVES VIA TRANS-APICAL ACCESS

CROSS-REFERENCE TO RELATED APPLICATION

This present application is a divisional application of U.S. patent application Ser. No. 13/397,545, filed on Feb. 15, 2012 and entitled "PERCUTANEOUS TRANSCATHETER REPAIR OF HEART VALVES VIA TRANS-APICAL ACCESS," which claims the benefit under 35 U.S.C. § 119(e) of U.S. Provisional Patent Application No. 61/492,279, filed on Jun. 1, 2011 and titled "TRANSCATHETER FIXATION OF ANNULOPLASTY RINGS," the disclosures of which are hereby incorporated by reference herein in their entireties.

TECHNICAL FIELD

The present disclosure relates to treating and repairing heart valves, and specifically to apparatus, systems, and methods for percutaneous transcatheter delivery and fixation of annuloplasty rings to repair heart valves. Disclosed embodiments are configured to be delivered through a catheter using a trans-apical approach.

BACKGROUND INFORMATION

Heart valve defects, such as regurgitation, may be caused by a relaxation of the tissue surrounding a heart valve (e.g., the mitral valve or tricuspid valve). This causes the valve opening to enlarge, which prevents the valve from sealing properly. Such heart conditions are commonly treated by a procedure during which an annuloplasty ring is fixed or secured around the valve. Cinching or securing the tissue to the ring can restore the valve opening to its approximate original size and operating efficiency.

Typically, annuloplasty rings have been implanted during open heart surgery, so the annuloplasty ring can be sewn into the valve annulus. Open heart surgery is a highly invasive procedure that requires connecting a heart and lung machine (to pump the patient's blood and breathe for the patient), stopping the patient's heart, and cutting open the thoracic cavity and heart organ. The procedure can expose the patient to high risk of infection and may result in a long and difficult recovery. The recovery can be particularly difficult for patients in less than optimal health due to the effects of suffering from a heart valve defect such as regurgitation.

SUMMARY OF THE DISCLOSURE

Disclosed herein are apparatus, systems, and methods for repairing heart valves through percutaneous transcatheter delivery and fixation of annuloplasty rings to heart valves via trans-apical access of the heart.

In certain embodiment, methods are disclosed for repairing a target heart valve through percutaneous transcatheter delivery and fixation of an annuloplasty ring to the annulus of the target heart valve via trans-apical access to the heart. A guiding sheath may be introduced into a ventricle of the heart through an access site at an apex of the heart. A distal end of the guiding sheath may be positioned retrograde through the target valve. The distal end and a distal portion of the guiding sheath are positioned within the atrium of the heart. An annuloplasty ring arranged in a compressed delivery geometry is inserted into the guiding sheath. The annuloplasty ring is positioned in the distal portion of the guiding sheath within the atrium of the heart. The distal end of the guiding sheath is retracted back through the heart valve and into the ventricle of the heart, thereby exposing the annuloplasty ring. The annuloplasty ring may be expanded from the delivery geometry to an operable geometry. Anchors of the annuloplasty ring may be deployed. The anchors may be configured to be pressed into and engage tissue of the annulus of the target valve. The guiding sheath can then be retracted from the access site of the heart.

In certain embodiments, a segmented annuloplasty ring may be arranged in a compressed delivery geometry. The annuloplasty ring may be compressed around a balloon assembly comprising an upper balloon, a lower balloon, a double lumen shaft, and a recess configured to accommodate the annuloplasty ring in the compressed delivery geometry. The upper balloon may define an upper surface of the recess and the lower balloon may define a lower surface of the recess. The double lumen shaft may have a first lumen coupled to and configured to direct a fluid or gas into the upper balloon from outside the heart and may have a second lumen coupled to and configured to direct a fluid or gas into the lower balloon from outside the heart. The annuloplasty ring and at least the upper balloon of the balloon assembly may be positioned through the guiding sheath and within the distal portion of the guiding sheath positioned within the atrium of the heart. The distal end of the guiding sheath may be retracted back through the heart valve and into the ventricle of the heart, thereby exposing the upper balloon, the lower balloon, the recess of the balloon assembly, and the annuloplasty ring. The upper balloon of the annuloplasty ring may be inflated, at least partially, to a diameter larger than the diameter of the annulus of the target valve. The lower balloon of the balloon assembly may be inflated, at least partially, to expand the annuloplasty ring from the delivery geometry to an operable geometry. The balloon assembly may be retracted to position the annuloplasty ring planar to a plane of the annulus of the target valve on an atrial surface of the annulus, such that the inflated upper balloon presses the annuloplasty ring against the annulus of the target valve.

In certain embodiments, annuloplasty rings are disclosed that include an outer hollow member including a plurality of segments. Adjacent segments cooperate with one another to allow the annuloplasty ring to expand from a compressed delivery geometry to an expanded operable geometry. The annuloplasty ring also includes an internal anchor member located at least partially within the outer hollow member. The internal anchor member includes a plurality of anchors configured to attach the annuloplasty ring to tissue of a heart valve annulus. The internal anchor member is configured to move the plurality of anchors with respect to a plurality of windows in the outer hollow member to selectively deploy the plurality of anchors through the respective windows.

In certain other embodiments, an annuloplasty ring includes anchors and one or more sutures attached to eyelets in the anchors. The one or more sutures may be configured to connect to the anchors through the guiding sheath. Deploying the anchors of the annuloplasty ring includes pulling one or more sutures as the annuloplasty ring is pressed against the target valve annulus. Pulling the one or more sutures may cause the anchors to deploy and/or engage the tissue of the annulus of the target valve.

BRIEF DESCRIPTION OF THE DRAWINGS

Understanding that drawings depict only certain embodiments and are not therefore considered to be limiting in nature, non-limiting and non-exhaustive embodiments of the disclosure are described and explained with additional specificity and detail through the use of the accompanying drawings.

FIGS. 11A and 11B are schematic diagrams illustrating a shape memory hypotube cut to form a plurality of segments for use as an outer tube of a segmented annuloplasty ring according to one embodiment.

FIG. 11C is a schematic diagram illustrating a cutting pattern used for laser processing the hypotube shown in FIGS. 11A and 11B.

FIGS. 13A and 13B are simplified schematics illustrating cross-section side views of an annuloplasty ring before (FIG. 13A) and after (FIG. 13B) deployment of the anchors shown in FIG. 12C according to one embodiment.

DETAILED DESCRIPTION OF PREFERRED EMBODIMENTS

The present disclosure provides apparatus, systems, and methods for repairing heart valves through percutaneous transcatheter delivery and fixation of annuloplasty rings to heart valves via trans-apical access of the heart. An annuloplasty ring that may be flexible and/or segmented can be configured in both a compressed delivery geometry that can be inserted into, and delivered through, a catheter tube and an expanded operable geometry providing a curved and rigid or semi-rigid annular shape. In certain embodiments, an annuloplasty ring may be delivered percutaneously to the mitral and/or tricuspid valve annulus of the heart via a trans-apical approach through a thoracotomy.

Certain annuloplasty rings disclosed herein are small and flexible enough to be percutaneously delivered into the heart through a catheter, and can be put into a rigid or semi-rigid ring shape and then securely anchored into the heart valve annulus. Disclosed embodiments enable trans-apical delivery methods and provide for anchoring and cinching the annuloplasty ring around the valve annulus.

Figure 1A:
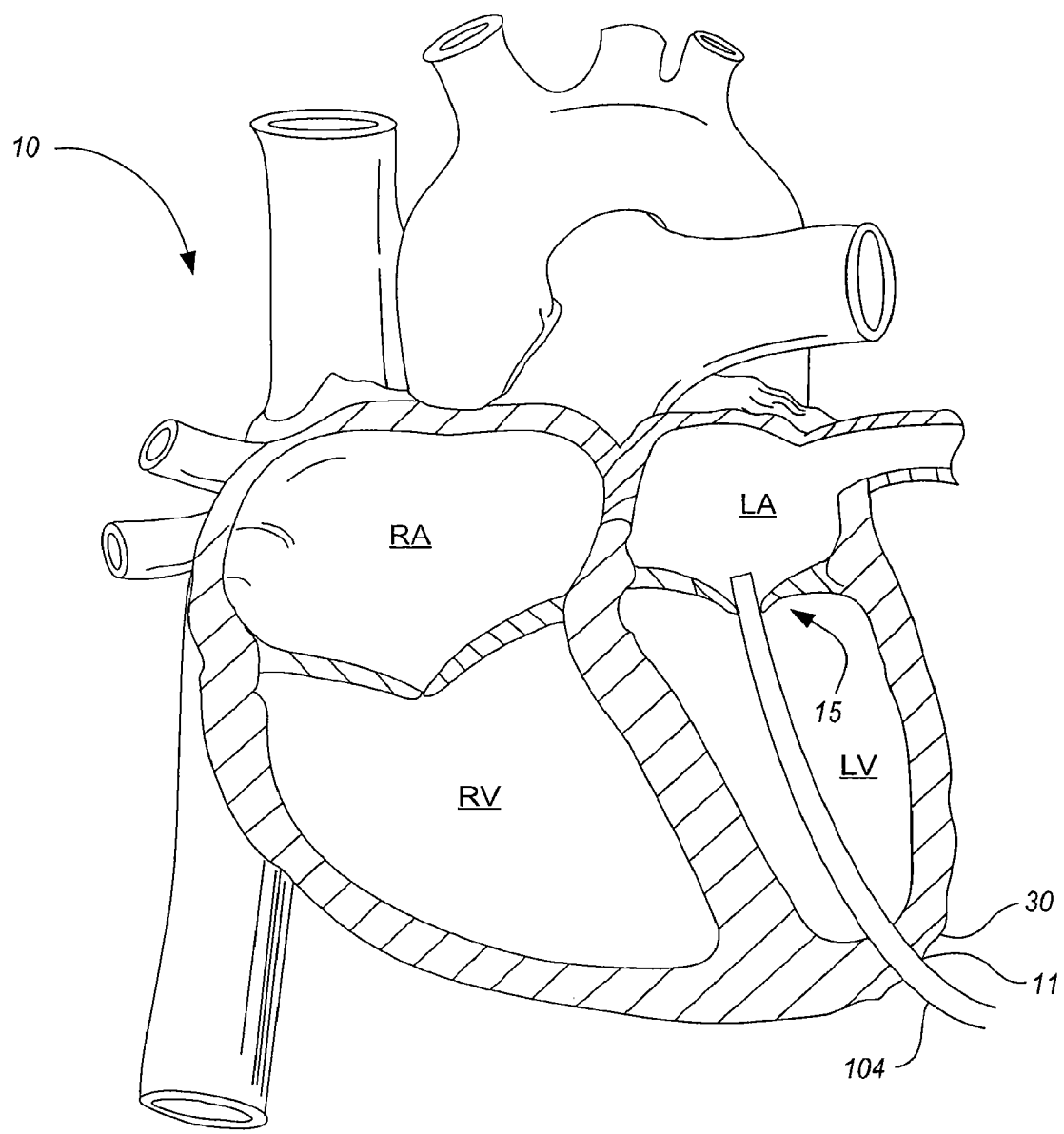
FIG. 1A illustrates a cross-sectional view of a heart accessed by a sheath via a trans-apical approach according to one embodiment.

FIG. 1A is a schematic diagram illustrating an example trans-apical approach for inserting an annuloplasty ring (not shown) through the mitral valve 15 of a heart 10 according to one embodiment. In this example, a guiding sheath 104 is shown passing through an access site 11 at the apex 30 of the heart 10, through the left ventricle LV, through the mitral valve 15, and into the left atrium LA. The annuloplasty ring may be delivered through the catheter 104 into the left atrium LA and anchored to an annulus of the mitral valve 15. In one embodiment, a needle or trocar may be used to puncture through the apex 30 to create a small opening through which a guidewire (not shown) can be inserted through the left ventricle LV into the left atrium LA. Then, the guidewire may be used to guide successively larger and stiffer catheters so as to gradually increase the size of the opening in the apex 30 of the heart 10.

As can be appreciated, a trans-apical approach to accessing the heart can be used to access other chambers of the heart, including, for example, the right ventricle RV and right atrium RA. Accordingly, subsequent figures do not depict the entire heart, but rather they merely depict a ventricle and an atrium. A person having ordinary skill in the art appreciates that the ventricle and atrium shown can be any two chambers of any heart that are separated by a valve, and that the valve can be accessed from a tip or apex of the heart proximate to the more "down-flow" of the two chambers of the heart.

Figure 1B:
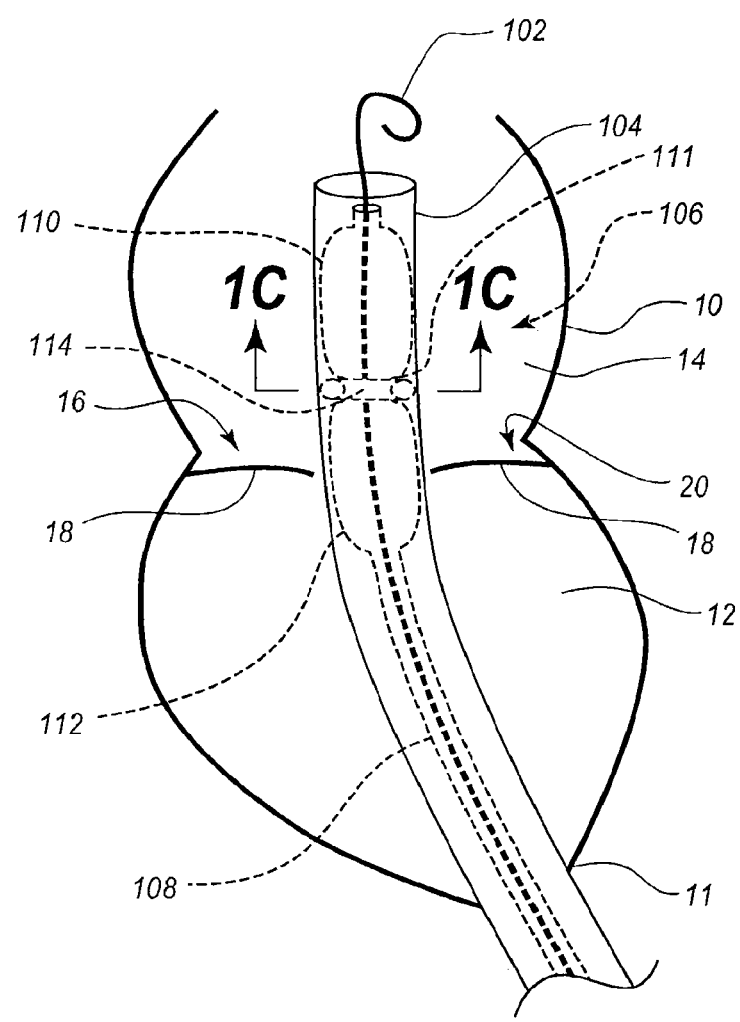
FIG. 1B illustrates a side view of a balloon assembly being delivered through a guiding sheath inserted into a ventricle of the heart via a trans-apical access according to one embodiment.

FIG. 1B illustrates a partial sectional side view of a balloon assembly 106, including an annuloplasty ring 114, being delivered via a trans-apical access site 11, according to one embodiment. A patient's heart 10 may be exposed minimally and/or visibly via a small thoracotomy, and the apex of the heart may be pierced with a needle to allow introduction of a guidewire 102. The guidewire 102 may be inserted through a ventricle chamber 12 of the heart 10, through a target valve 16 of the heart 10, and into an atrium 14 chamber of the heart 10. A guiding sheath 104 can be inserted over the guidewire 102 and also into the atrium chamber 14 of the heart 10. The size of the guiding sheath 104 may be, for example, between approximately 18 Fr and 24 Fr (approximately 6 mm to 8 mm) in diameter to accommodate the balloon assembly 106. As shown, the guiding sheath 104 may be positioned retrograde through leaflets 18 of the target valve 16.

The balloon assembly 106 can be inserted over the guidewire 102 and through the guiding sheath 104. The balloon assembly 106 may include a shaft 108, an upper balloon 110, and a lower balloon 112. A recess 111 (or narrow waist) between the upper balloon 110 and the lower balloon 112 accommodates and secures the annuloplasty ring 114 on the balloon assembly 106. In FIG. 1B, the annuloplasty ring 114 is in a compressed delivery geometry around the recess 111 of the balloon assembly 106. In the delivery geometry, the plane of the annuloplasty ring 114 may be transverse to a major axis of the guiding sheath 104 and substantially parallel to a plane of an annulus 20 of the target valve 16.

Figure 1C:
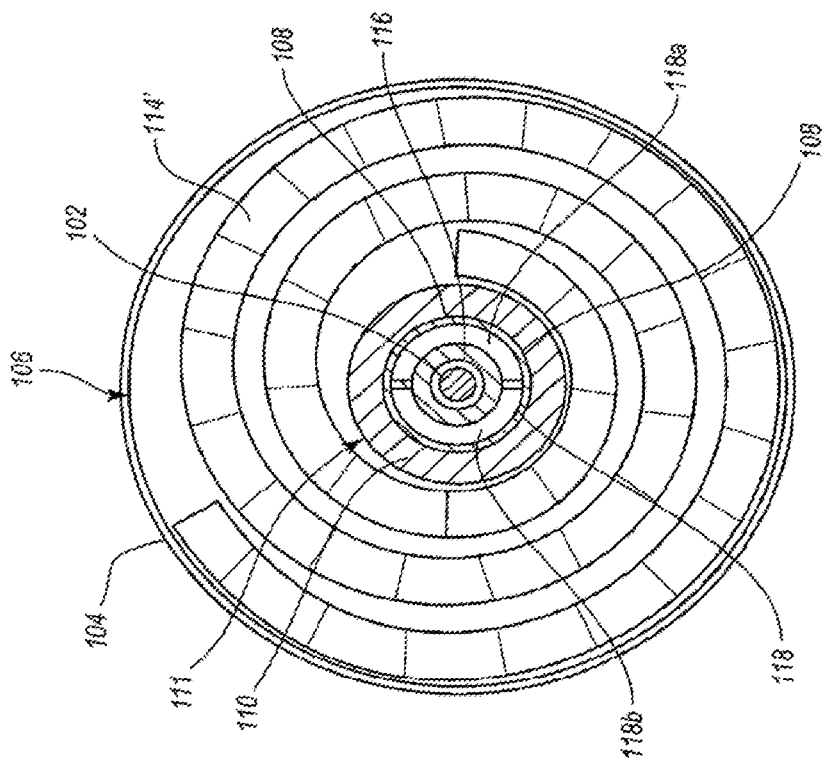
FIG. 1C illustrates a cross-sectional top view of the balloon assembly within the guiding sheath, portraying a delivery configuration of an annuloplasty ring according to one embodiment.

FIG. 1C illustrates a cross-sectional view of the balloon assembly 106 of FIG. 1B within the guiding sheath 104, according to one embodiment. FIG. 1C portrays a delivery configuration of the annuloplasty ring 114 positioned in the recess 111 of the balloon assembly 106 as it is delivered through the guiding sheath 104. The annuloplasty ring 114 may be segmented to enable it to fold over itself around the balloon assembly 106 in a delivery geometry. The annuloplasty ring 114 may be compressed and folded within a plane transverse to a longitudinal axis of the guiding sheath 104.

FIG. 1C also depicts a cross-section of the shaft 108 of the balloon assembly 106. The shaft 108 includes a guidewire lumen 116 and a double inflation lumen 118. The guidewire lumen 116 of the balloon assembly 106 is over the guidewire 102. The double inflation lumen 118 includes an upper balloon inflation portion 118 *a* and a lower balloon inflation portion 118 *b*. The double inflation lumen 118 may allow the upper balloon (see FIG. 1B) and the lower balloon 112 to be separately inflated. The upper balloon inflation portion 118 *a* and lower balloon inflation portion 118 *b* are defined by an inner 118 *d* and outer 118 *c* layer separated into the two portions by a bisecting material 118 *e*. The annuloplasty ring is positioned around the shaft 108 and portions of the lower balloon 112, in the recess 111 of the balloon assembly 106. For sake of clarity, only a portion of the lower balloon 112 is shown.

In another embodiment, a portion of an upper balloon may be positioned within the recess 111 and configured to expand when inflated to expand the annuloplasty ring. In another embodiment, the lower balloon inflation portion 118*b* may end below the recess 111, such that it would not be visible in the cross-section of FIG. 1C. As can be appreciated, other configurations of a double inflation lumen are possible.

In another embodiment, the balloon assembly 106 comprises a single balloon including an upper balloon portion (e.g., upper balloon 110 shown in FIG. 1B) and a lower balloon portion (e.g., lower balloon 112 shown in FIG. 1B) that are more pliant than a recess portion (e.g., recess 111 shown in FIG. 1B) of the balloon. The recess portion may be more rigid (e.g., formed of a thicker portion of material forming the balloon assembly 106) than the upper balloon and lower balloon portions. A single inflation lumen 118 may be used to inflate both the upper balloon portion of the balloon assembly 106 and the lower balloon portion of the balloon assembly 106. The more pliant upper and lower balloon portions may be configured to inflate more readily than the recess portion and, thus, may inflate more rapidly and/or readily than (e.g., before or prior to) the recess portion. Inflation (and expansion) of the upper balloon portion more rapidly than inflation (and expansion) of the recess portion may restrict distal shifting of the annuloplasty ring relative to the recess portion, for example, as the delivery assembly is advanced and positioned in a target valve. Similarly, inflation (and expansion) of the lower balloon portion more rapidly than inflation (and expansion) of the recess portion may restrict proximal shifting of the annuloplasty ring relative to the recess as the delivery assembly is advanced and positioned in the target valve. Inflation of the balloon assembly may cause expansion of the upper balloon portion and the lower balloon portion initially, and eventually expansion of the recess portion. Expansion of the recess portion may expand the annuloplasty ring from the compressed delivery geometry to an expanded operable geometry.

Figure 1D:
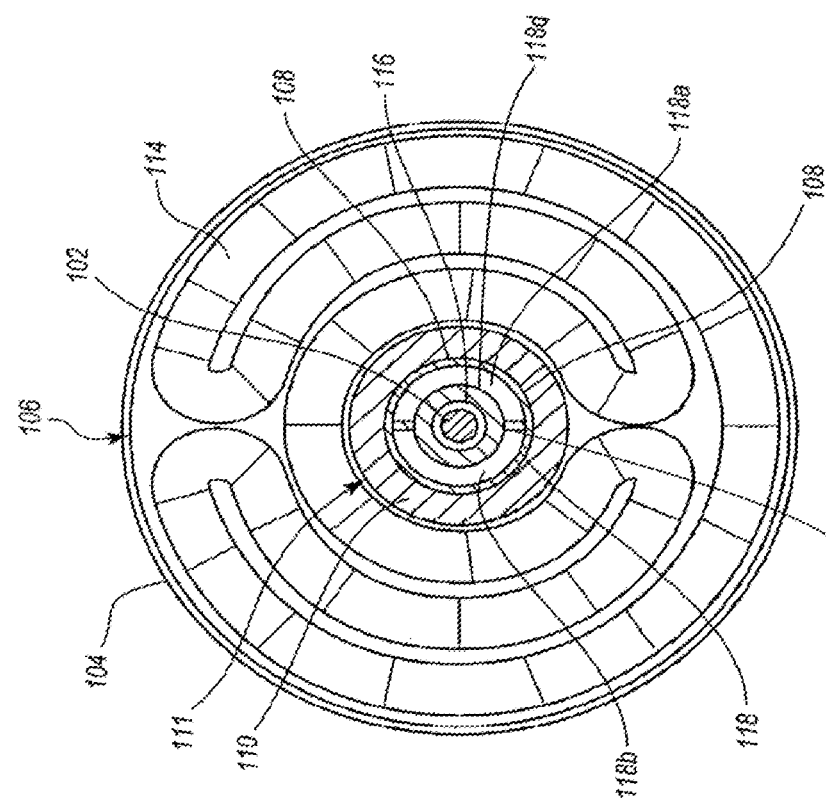
FIG. 1D illustrates a cross-sectional top view of the balloon assembly within the guiding sheath, portraying a delivery configuration of an annuloplasty ring according to another embodiment.

FIG. 1D illustrates a cross-sectional top view of the balloon assembly within the guiding sheath 104, portraying a delivery geometry of an annuloplasty ring 114', according to another embodiment. In the embodiment of FIG. 1D, the annuloplasty ring 114' is configured to have two ends that are separated and configured to snap together to form the ring-shape of the annuloplasty ring 114'. Because the ends are separated, the annuloplasty ring, in the compressed delivery geometry, can be wound around the shaft 108 of the balloon assembly and within the recess 111 in a spiral fashion, as shown. The annuloplasty ring 114' is compressed (e.g., wound in a spiral) within a plane transverse to a longitudinal axis of the guiding sheath 104. The annuloplasty ring 114' may be formed of a shape memory material configured to restrict expansion of the annuloplasty ring 114' beyond a shape that would allow undesired disconnection or separation from the recess 111 of the balloon assembly.

FIGS. 1C and 1D provide example embodiments of an annuloplasty ring and a delivery geometry. A person having ordinary skill in the art appreciates that other delivery geometries are possible.

Figure 2:
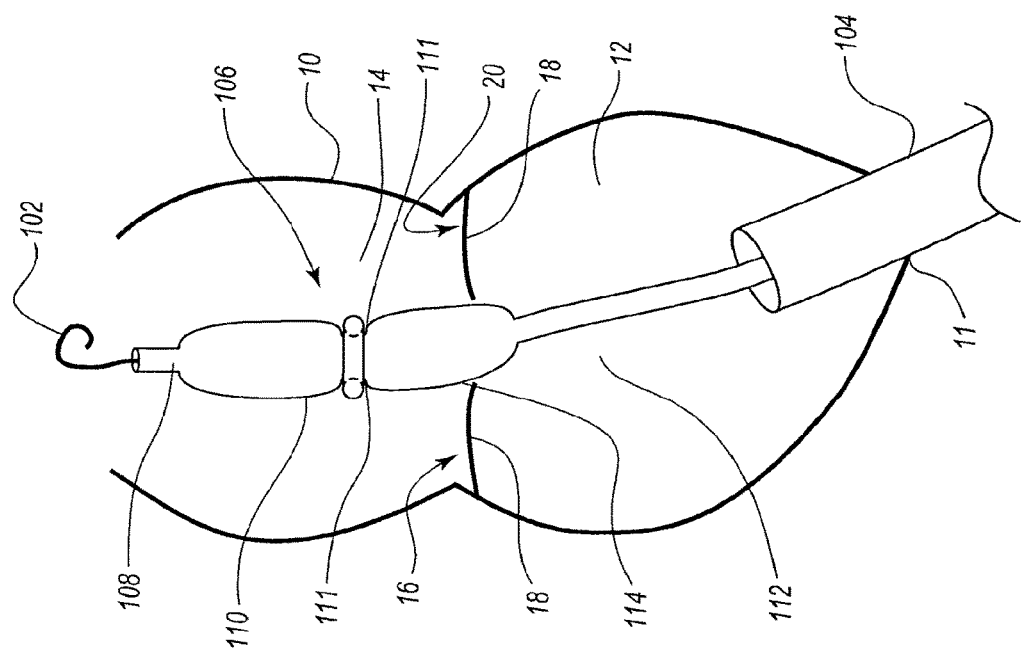
FIG. 2 illustrates the guiding sheath retracted through the target valve exposing the balloon assembly of FIG. 1B

FIG. 2 illustrates the guiding sheath 104 retracted back through the target valve 16 to expose the balloon assembly 106. The upper balloon 110, the lower balloon 112 and the recess 111, in which the annuloplasty ring 114 is disposed, are exposed outside of and distal to the distal end of the guiding sheath 104. The guiding sheath 104 may be retracted, but not removed from the heart 10 during the procedure to provide a channel by which the balloon assembly 106 can be removed from the heart 10 and to maintain access to the target valve 16 should the annuloplasty ring 114 need to be retrieved during the procedure.

Figure 3:
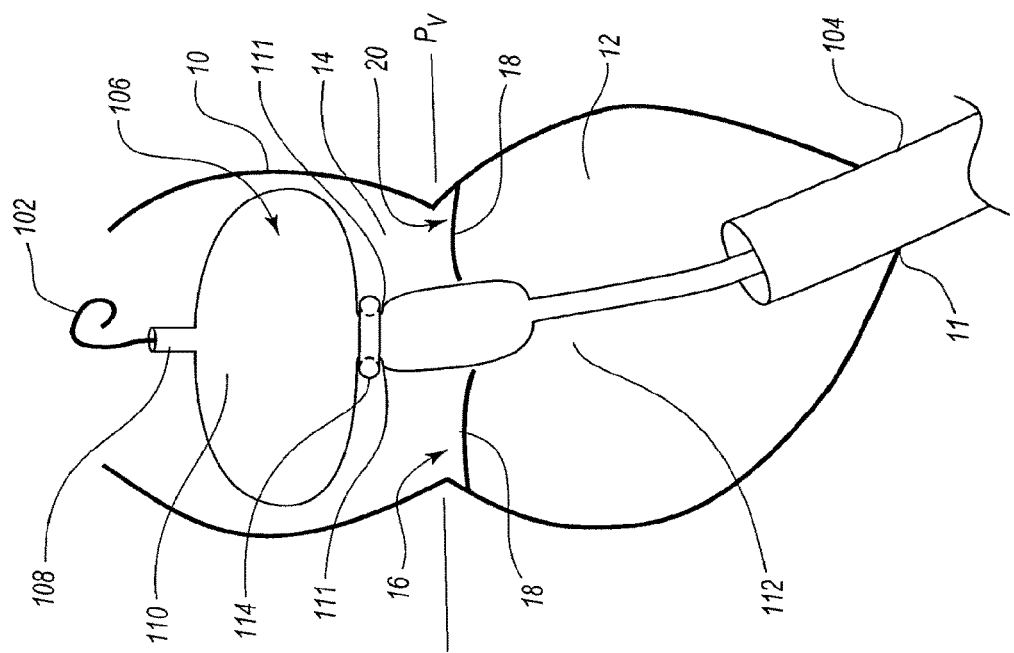
FIG. 3 illustrates the balloon assembly of FIG. 1B with the upper balloon inflated.

FIG. 3 illustrates the balloon assembly 106 of FIG. 1B with the upper balloon 110 inflated. The upper balloon 110 may be inflated first to secure the position of the annuloplasty ring 114 relative to the target valve 16. Inflation of the upper balloon 110 may limit undesired shifting of the annuloplasty ring 114 in a distal direction (toward the end of the balloon assembly and further into the atrium 14), particularly during anchoring of the annuloplasty ring 114. Furthermore, inflation of the upper balloon 110 may prevent the annuloplasty ring 114 from popping off (or similarly separating from) the balloon assembly 106 during expansion of the annuloplasty ring 114, so that the annuloplasty ring 114 cannot be inadvertently separated from the balloon assembly 106 prior to anchoring and left to float undesirably in the atrium 14 of the heart 10. Inflation of the upper balloon 110 may be sufficient such that a size (e.g. diameter) of the upper balloon 110 provides a surface to allow a practitioner to pull back on the balloon assembly 106 without drawing the balloon assembly 106 through the target valve 16.

Inflation of the upper balloon 110 to a size larger than the diameter of the annulus of the target valve allows the practitioner to exert a force against the atrial surface of the annulus 20 of the target valve 16. The practitioner can pull back the upper balloon 110 of the balloon assembly 106 against the annulus 20, enabling a positioning force to be applied to the annuloplasty ring 114. The positioning force can be applied by a practitioner to determine proper positioning of the annuloplasty ring 114 for anchoring. The positioning force against the annuloplasty ring 114 may also press the annuloplasty ring 114 against the annulus 20 and prevent undesired shifting of the annuloplasty ring 114 during anchoring.

Figure 4:
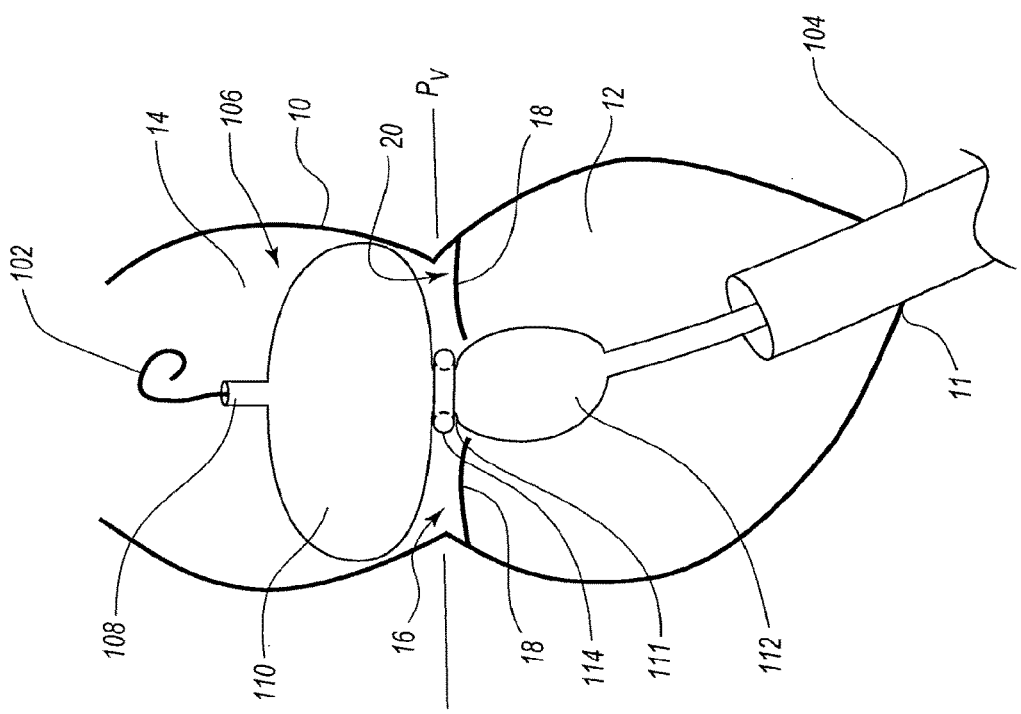
FIG. 4 illustrates an upper balloon of the balloon assembly of FIG. 1B inflated and retracted to guide and/or secure the position of the annuloplasty ring relative to the annulus of the target valve.

FIG. 4 illustrates the upper balloon 110 of the balloon assembly 106 of FIG. 1B inflated to secure the position of the annuloplasty ring 114 relative to the annulus 20 of the target valve 16 and the balloon assembly 106 retracted such that the annuloplasty ring 114 is positioned at the level of the annulus 20 of the target valve 16. The annuloplasty ring 114 is oriented so as to be planar to the plane $P_v$ of the target valve 16, on the atrial surface of the target valve 16. The upper balloon 110 and the annuloplasty ring 114 are positioned within the atrium 14 of the heart, above the target valve 16. As illustrated, the inflated upper balloon 110 may restrict proximal movement of the balloon assembly with respect to the target valve 16. Movement of the inflated upper balloon 110 through the target valve 16 may be impeded by the size of the inflated upper balloon 110 relative to a diameter of the annulus 20 of the target valve 16.

Figure 5:
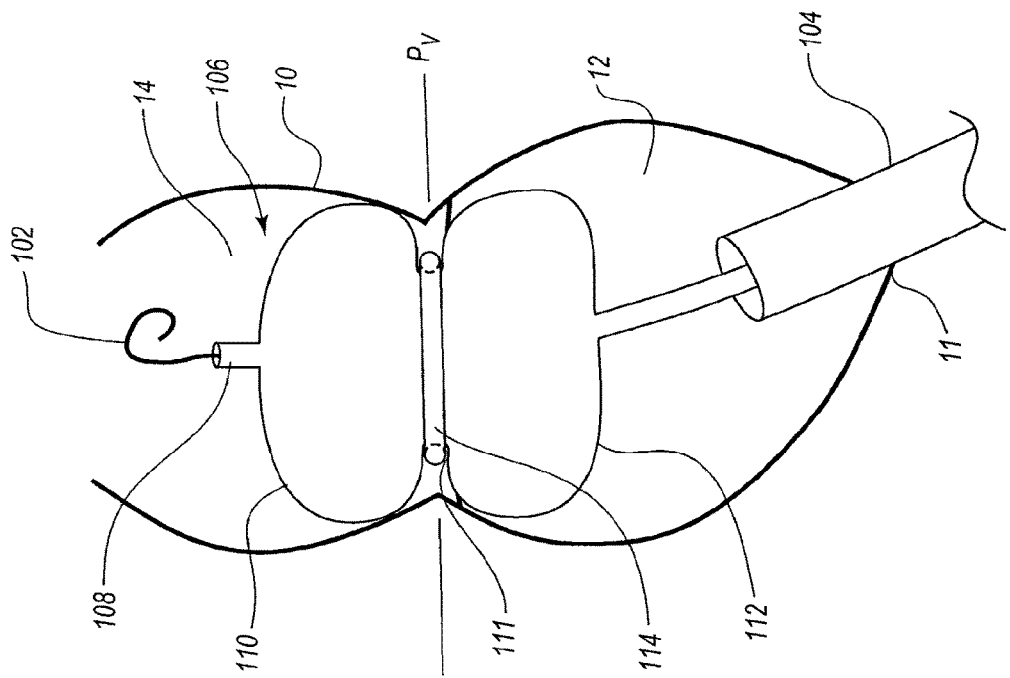
FIG. 5 illustrates the upper balloon and a lower balloon of the balloon assembly of FIG. 1B inflated to expand a diameter of the annuloplasty ring.

The lower balloon 112 can be inflated to expand the annuloplasty ring 114 from the compressed delivery geometry to an expanded operable geometry. FIG. 5 illustrates the upper balloon 110 and the lower balloon 112 of the balloon assembly 106 of FIG. 1B partially inflated to expand the annuloplasty ring 114. The upper balloon 110 and lower balloon 112 may be further expanded together to further transition the annuloplasty ring 114 from the delivery geometry to the operable geometry. Inflation of the balloons 110, 112 may increase the circumference of the recess 111, causing the annuloplasty ring 114 to, for example, unfold or otherwise expand. In certain other embodiments, the annuloplasty ring 114 may comprise shape memory material configured to automatically transition (or spring) back to an operable geometry upon retraction of the guide catheter past the annuloplasty ring 114.

Figure 6:
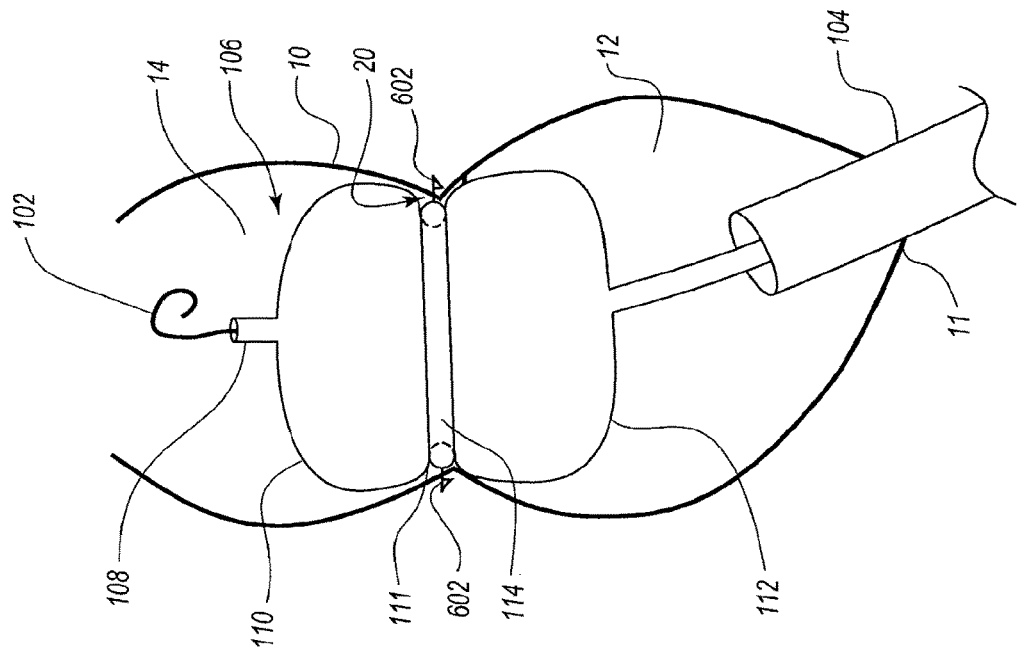
FIG. 6 illustrates deployment of the anchors of the annuloplasty ring of the balloon assembly of FIG. 1B.

FIG. 6 illustrates deployment of anchors 602 of the annuloplasty ring 114. The anchors 602 may be barbed prongs configured to protrude from the annuloplasty ring 114. In certain embodiments, the anchors 602 may be deployed automatically as the annuloplasty ring 114 expands, similar to one or more embodiments of annuloplasty rings discussed below. In certain other embodiment, the anchors 602 may be deployed by a practitioner, similar to one or more embodiments of annuloplasty rings discussed below.

Figure 7:
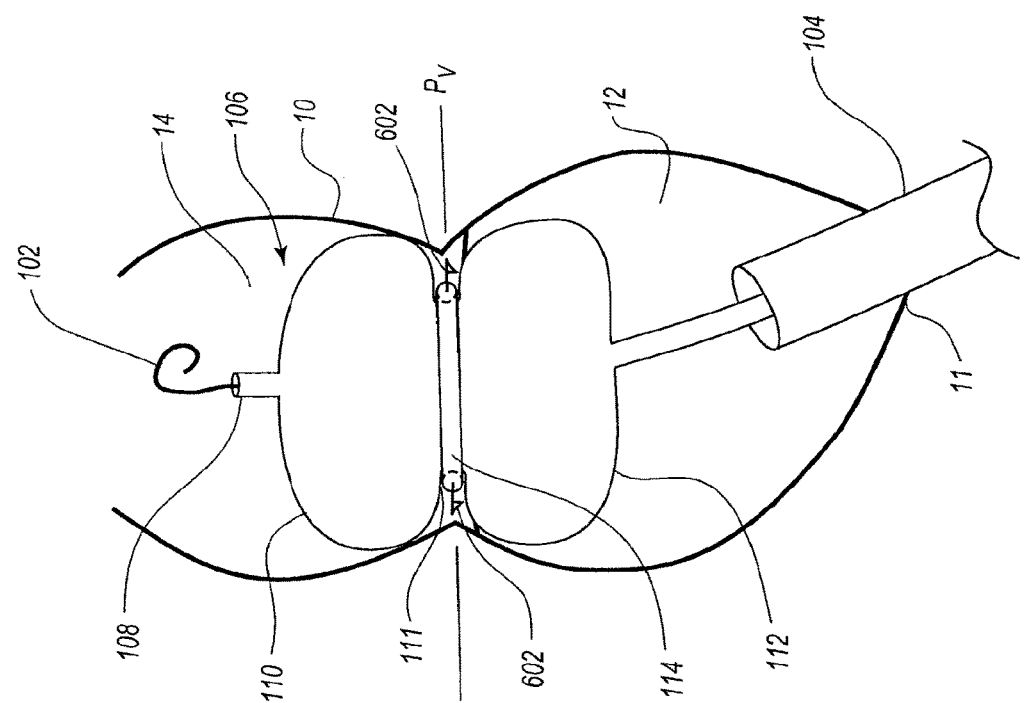
FIG. 7 illustrates anchoring of the annuloplasty ring of FIG. 1B.

FIG. 7 illustrates anchoring of the annuloplasty ring of FIG. 1B. The upper balloon 110 and the lower balloon 112 may be further inflated to further expand the annuloplasty ring 114 and drive the anchors 602 into the tissue of the annulus 20. As can be appreciated, in other embodiments, inflation of either the upper balloon 110 or the lower balloon 112 alone may be sufficient to expand the annuloplasty ring 114.

Figure 8:
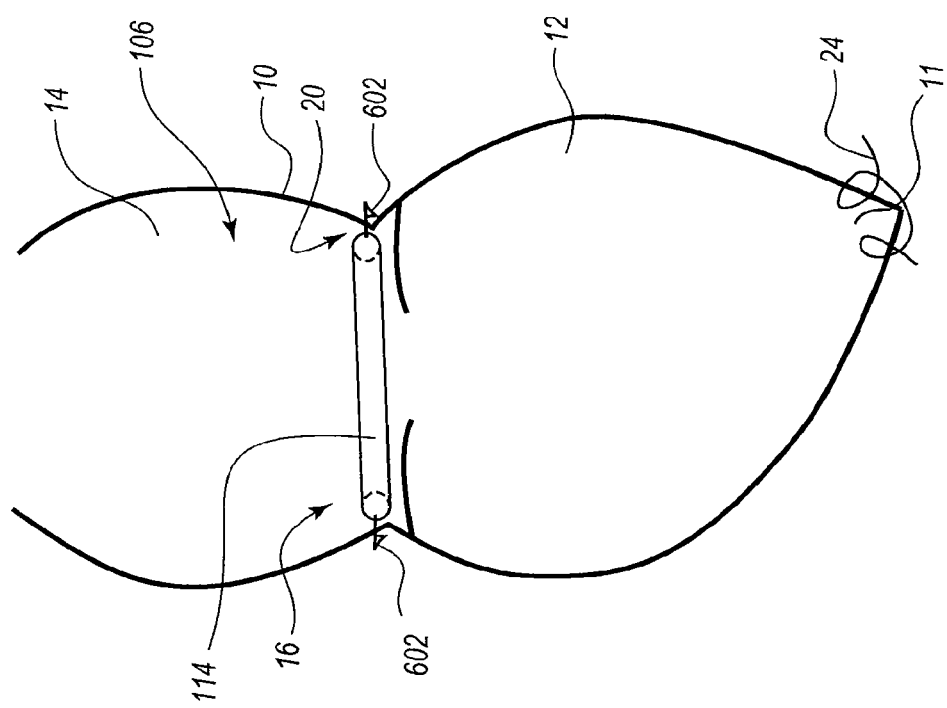
FIG. 8 illustrates the annuloplasty ring of FIG. 1B anchored into the annulus of the target valve, the balloon assembly, guiding sheath, and guidewire removed, and the heart access site closed.

FIG. 8 illustrates the annuloplasty ring 114 anchored into the annulus 20 of the target valve 16. If the annuloplasty ring 114 is appropriately positioned, for example, secured to the annulus 20 on the plane $P_v$ of the target valve 16, or as otherwise desired by the practitioner, then the balloon assembly 106 may be withdrawn and/or otherwise removed, leaving the annuloplasty ring 114 anchored in place at the target valve 16. The annuloplasty ring 114 may then be cinched, snapped together, or otherwise reduced in diameter to reduce a diameter of the annulus 20 of the target valve 16 to treat regurgitation. Reducing the diameter of the annulus may improve the coaptation of the leaflets such that a gap between the leaflets sufficiently closes during left ventricular contraction, thereby treating regurgitation. Cinching the annuloplasty ring, snapping together free ends of the annuloplasty ring, and other methods of reducing the diameter of the ring once it is implanted are discussed below in greater detail. The guiding sheath 104 and the guidewire 102 can also be removed and the heart access site 11 can be closed, for example, with one or more sutures 24.

Figure 9A:
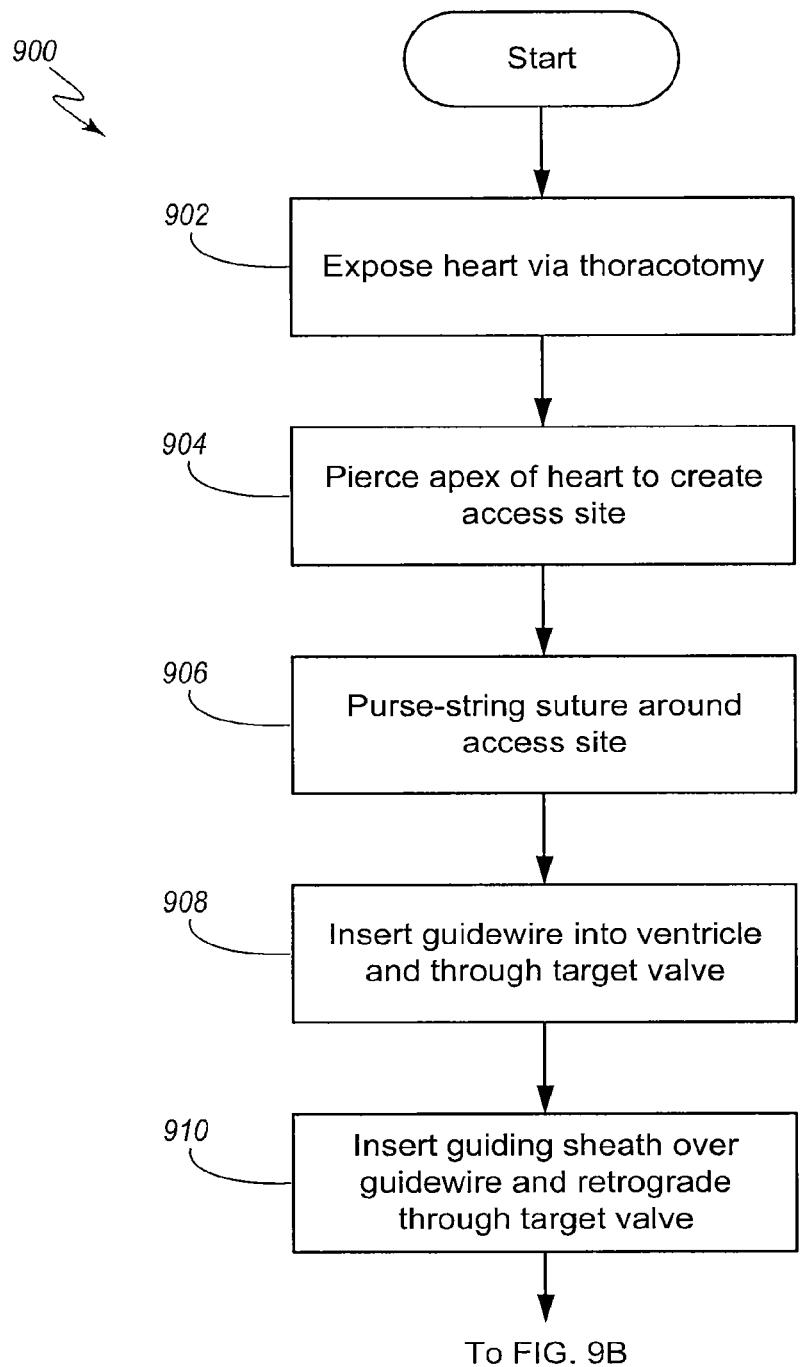
FIGS. 9A, 9B, and 9C are a flow diagram of a method for repairing a target heart valve through percutaneous transcatheter delivery and fixation of an annuloplasty ring to the target heart valve via trans-apical access of the heart according to one embodiment.
Figure 9B:
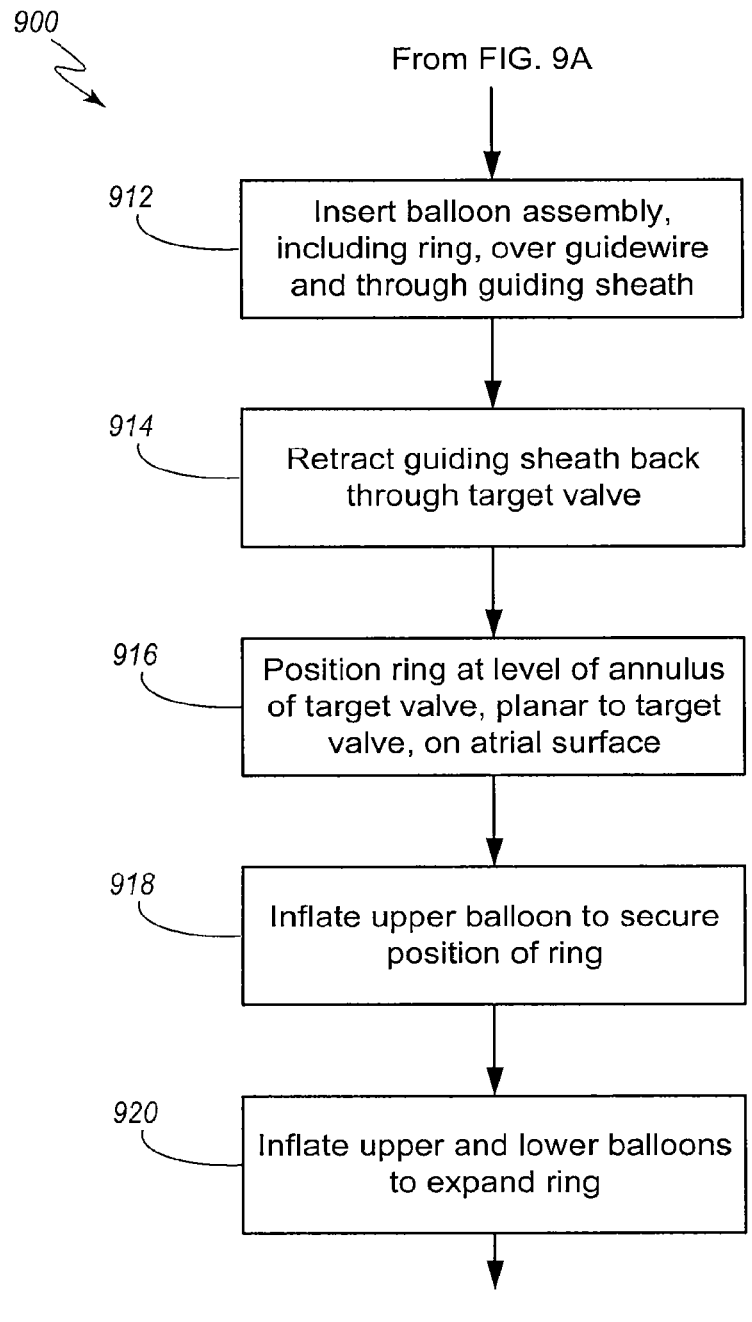
Figure 9C:
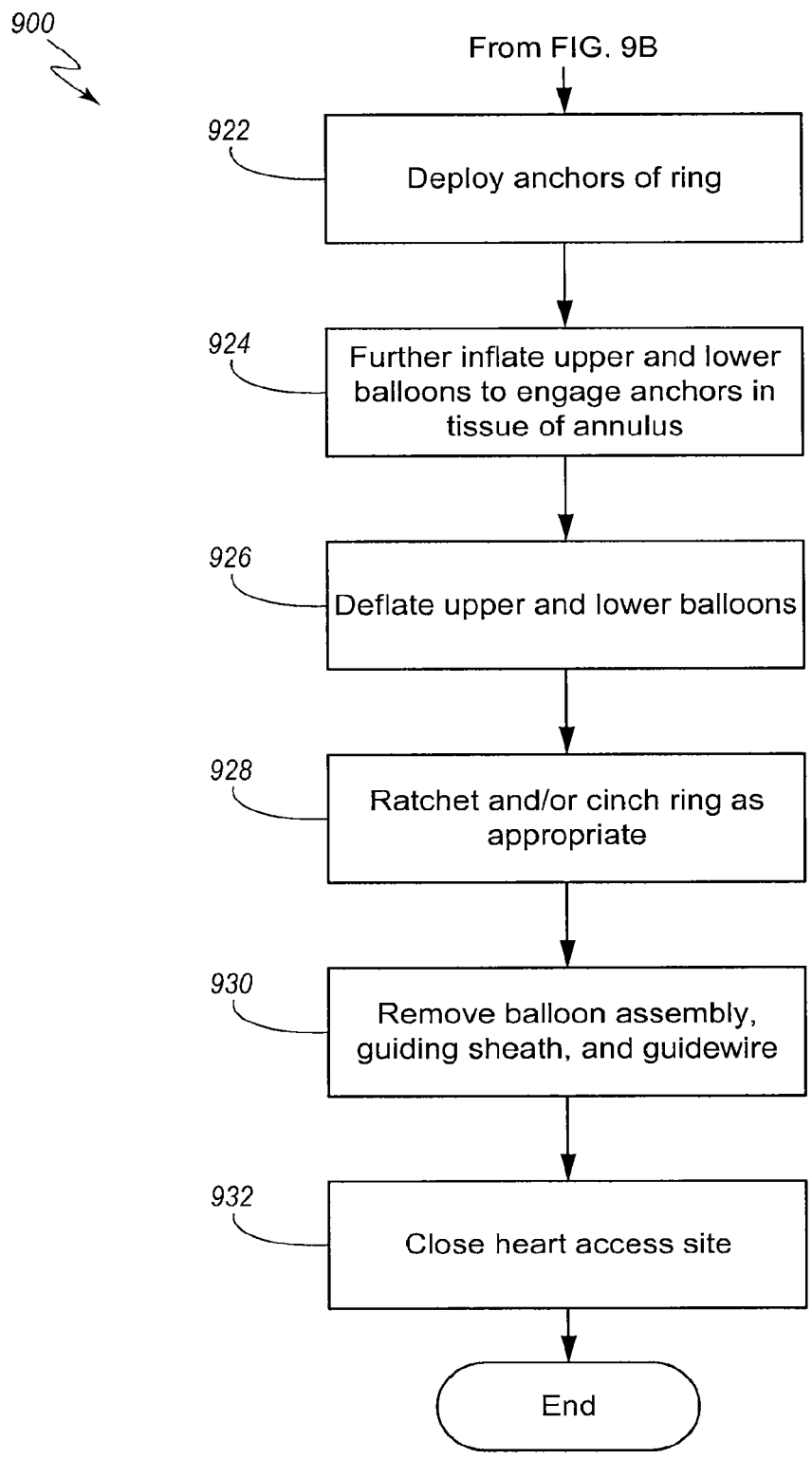

FIGS. 9A, 9B, and 9C are a flow diagram of a method 900 for repairing a target heart valve through percutaneous transcatheter delivery and fixation of an annuloplasty ring to the target heart valve via trans-apical access of the heart. As provided in FIG. 9A, the heart may be exposed 902, for example, via a thoracotomy done at the fifth or sixth rib of a patient, where the pulse of the heart can be felt on the chest of the patient. A mini-retractor may be positioned at the thoracotomy to maintain patency of the thoracotomy opening. A needle may be used to pierce 904 the apex of the heart to create an access site into the heart. The access site may access a ventricle chamber of the heart, for example, in a human patient. One or more sets of purse-string sutures may be inserted 906 around the access site so as to provide a way to nearly immediately close the access site should there be an emergency or other need to quickly close the opening of the access site into the heart. A guidewire may be inserted 908 into the heart, for example into a ventricle, and through the target valve into an atrium of the heart. The guidewire may guide, or otherwise facilitate, insertion of other components to complete the desired valve repair procedure. For example, the guidewire may guide insertion 910 of a guiding sheath into the heart. The guiding sheath may be inserted 910 over the guidewire and retrograde through the target valve into the atrium chamber of the heart. As described above, the guiding sheath may have a diameter in a range of 18 Fr to 24 Fr. Accordingly, insertion of the guiding sheath over the guidewire may include multiple steps of inserting a dilator over the guidewire to dilate the access site, inserting a larger sheath, and then repeating.

Referring now to FIG. 9B, a delivery assembly, such as a balloon assembly, including an annuloplasty ring in a delivery geometry, may be inserted 912 over the guidewire and through the guiding sheath into a distal portion of the guiding sheath positioned within the atrium. An example of an insertion 912 of a balloon assembly, including an annuloplasty ring, is shown in FIG. 1B. With the balloon assembly positioned within the atrium of the heart, the guiding sheath may be retracted 914 back through the target valve to expose the balloon assembly. The ring may be positioned 916 at the level of the annulus of the target valve, planar to the plane of the target valve, above the atrial surface of the target valve. An upper balloon of the balloon assembly may be inflated 918 to guide and/or secure appropriate positioning of the annuloplasty ring proximate the annulus of the target valve. The upper balloon and lower balloon may be concurrently and/or simultaneously inflated 920 to expand the diameter of the annuloplasty ring and/or to transition the annuloplasty ring from the delivery geometry to an operable geometry. Inflation of the upper balloon alone may not cause substantial expansion of a recess formed between the upper balloon and the lower balloon. The balloon assembly may be configured such that inflation of the lower balloon, or concurrent inflation of the upper balloon and lower balloon results in expansion of the recess (or waist) of the balloon assembly.

Referring now to FIG. 9C, the anchors of the annuloplasty ring are deployed 922. In certain embodiments, the anchors may deploy automatically with expansion of the annuloplasty ring (and/or with transition of the annuloplasty ring from the delivery geometry to the operable geometry). In certain other embodiments, a practitioner may be enabled to control deployment of the anchors. Once the anchors are fully deployed, the anchors (and the annuloplasty ring) can be implanted into the tissue of the annulus. The upper and lower balloons may be further inflated 924 to cause the annuloplasty ring to further expand and drive the anchors into the tissue of the annulus of the target valve and allow the anchors to engage the tissue of the annulus. The anchors engage the tissue of the annulus implants and secure the annuloplasty ring to the target valve. The upper and lower balloons can be deflated 926, for example to test securement of the annuloplasty ring and/or to prepare for removal of the balloon assembly from the heart. Proper implantation and/or securement of the annuloplasty ring in the target valve can enable repair of the target valve. The annuloplasty ring can be ratcheted and/or cinched 928 to decrease the diameter of the annuloplasty ring, and in turn the annulus of the target valve, which can allow the valve leaflets to function properly, eliminate regurgitation, and repair the valve. The balloon assembly, the guiding sheath, and the guidewire can be removed 930 from the heart through the access site. Then the heart access site can be closed 932, using for example the purse-string sutures and/or other closure mechanism or method.

Example Anchor Deployment Mechanism

Figure 10:
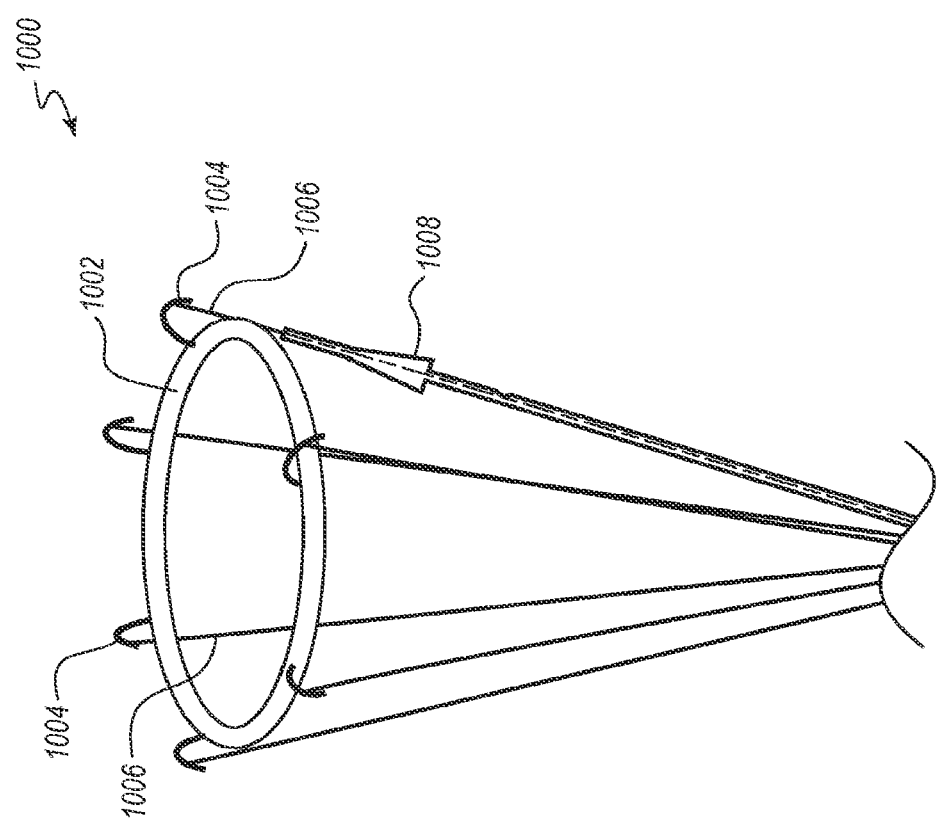
FIG. 10 illustrates an annuloplasty ring anchor deployment system according to one embodiment.

FIG. 10 illustrates an annuloplasty ring anchor deployment system 1000, according to one embodiment. In the illustrated embodiment, the annuloplasty ring 1002 includes a plurality of fish hook shaped, curved anchors 1004. Each of the plurality of anchors 1004 includes a laser hole (not shown), or other eyelet-type opening, on the anchor 1004. A suture 1006 may be coupled to the laser hole of each of the anchors 1004. The sutures 1006 may be formed of, for example, nylon, prolene, or the like. The plurality of sutures 1006 coupled to the laser hole may pass through the guiding sheath and out of the patient's body where they can be manipulated by a practitioner. For example, the practitioner may be able to pull the sutures 1006 to deploy the anchors and/or to drive the tips of the anchors into tissue.

A knot pusher 1008 may be disposed on the sutures 1006 to knot and cut the sutures 1006 once the anchors are deployed. With the annuloplasty ring forced down by an upper balloon of a balloon assembly or pulled down via the catheter onto the annulus, exposed anchors 1004 may start penetrating surrounding tissue of the annulus of the target valve. A practitioner can grip each suture 1006, for example, in sequence and attach the knot pusher 1008 with a clip attached to a small ancillary catheter. The ancillary catheter can be advanced along a presently gripped suture 1006 to advance a knot (e.g., a loop in the suture), sliding it to an appropriate securement position, and tighten the knot. For example, the knot may be advanced toward the base of the annuloplasty ring 1002. Once the knot is snug against the annuloplasty ring 1002, the knot may be tightened and a miniature clip may secure in place and cut the suture at the level of the annuloplasty ring 1002. The annuloplasty ring 1002 is thereby secured via both tissue penetration by the anchors 1004 and added sutures 1006 with knots. As another example, the knot may be advanced to an access site of the suture 1006 and/or anchor 1004 into the surrounding tissue of the annulus of the target valve. The knot may then be tightened against the base of the anchor 1006 and/or the tissue to secure the anchor in the tissue.

In another embodiment, the knot pusher 1008 may advance a fastener (rather than a loop in the suture 1006) disposed on the suture. The fastener may have an internal lumen extending axially therethrough and one or more engagement member(s) formed, for example, on an end of the lumen and/or the fastener. Between the engagement members may be defined an engagement aperture that may align with or otherwise be in communication with, for example, a lumen of an ancillary catheter, which may be configured to deploy the fastener. The engagement aperture may be sized to receive the suture 1006. Prior to deployment, the engagement member(s) may be deflected radially away (e.g., outward) from the axis of the fastener such that the engagement aperture has a relatively large first diameter sufficient to permit the suture 1006 to slide therethrough. Accordingly the fastener can move relative to the suture 1006 to be advanced and/or withdrawn along the suture 1006.

After the suture 1006 has been retracted or otherwise drawn taught to deploy the anchors 1004, the fastener may be deployed. Upon deployment the fastener may be, for example, detached from the ancillary catheter and the engagement members may be urged or permitted to spring back (e.g., inward) toward the axis of the fastener such that the engagement aperture assumes a second smaller diameter compressing and securing the suture 1006 in place. Preferably the engagement member(s) tend to spring toward a natural position at or toward the axis of fastener. Each engagement member may further include a pointed tip that, when the engagement member(s) are in the deployed position, engages and restricts movement of the fastener relative to the suture 1006. The fastener in the deployed position may resist proximal movement relative to the suture 1006, while allowing advancement distally to a desired position along the suture 1006, thereby providing a securement mechanism. The fastener may operate similar to Chinese handcuffs, allowing movement in one direction while restricting movement in the opposite direction. In another embodiment, a deployed fastener may resist both proximal and distal movement relative to the suture 1006. The fastener may be manufactured from a variety of materials including, for example, Nickel-Titanium (e.g., nitinol) alloys, shape-memory alloys, stainless steel, titanium, various plastics, and other biologically-compatible materials. The ancillary catheter may provide a cutting mechanism to cut the suture 1006 (e.g., cut off the excess of the suture 1006) once the fastener is appropriately positioned.

Example Ring Embodiments with Curved Anchors

Figure 11:
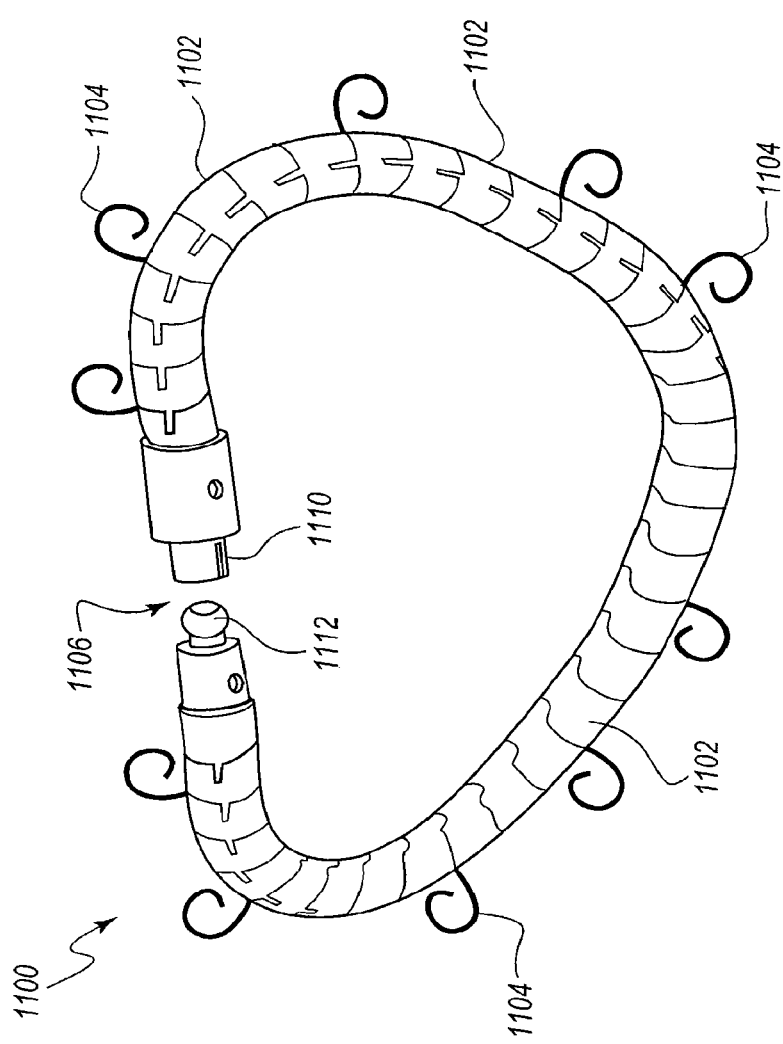
FIG. 11 is a simplified schematic diagram illustrating a perspective view of a segmented annuloplasty ring according to one embodiment.

FIG. 11 is a simplified schematic diagram illustrating a perspective view of a segmented annuloplasty ring 1100 according to one embodiment. Additional ring embodiments and discussion of the same may be found in U.S. patent application Ser. No. 13/198,582, which is hereby incorporated herein by reference in its entirety. The segmented annuloplasty ring 1100 may include a plurality of segments 1102, a plurality of anchors 1104, and a ring closure lock 1106. In FIG. 11, as well as in other embodiments disclosed herein, the plurality of segments 1102 are arranged in a "D-shape" in the operable geometry (e.g., when implanted around the annulus). The D-shaped ring 1100 has a certain geometrical ratio that is in conformance with the anatomical geometry of the human mitral valve annulus. For example, the ratio in certain embodiments of the anterior-posterior (A-P) distance to the commissure-commissure (C-C) distance of the ring 1100 when implanted is in a range between about 0.60 and about 0.70. In one embodiment, the implanted ratio of the A-P distance to the C-C distance is about 0.62. Artisans will recognize from the disclosure herein, however, that other operable geometries may also be used. For example, circular or oval operable geometries may be used. By way of example only, and not by limitation, the table below provides some example dimensions.

| Ring Implant Shape (mm) | | | |
|---|---|---|---|
| Size | C-C | AP | Ratio |
| 28 | 28.00 | 17.36 | 0.62 |
| 30 | 30.00 | 18.60 | 0.62 |
| 32 | 32.22 | 18.94 | 0.62 |
| 34 | 34.00 | 21.08 | 0.62 |
| 36 | 36.00 | 22.32 | 0.62 |

In addition to the operable geometry, the plurality of segments 1102 allow the ring 1100 to be placed in a compressed delivery geometry such that the ring 1102 can be disposed in a recess of a balloon assembly or other delivery assembly and positioned through a catheter into the heart. As discussed in detail below, in certain embodiments, the segmented annuloplasty ring 1100 includes a shape memory (e.g., Nitinol) hypotube into which the plurality of segments 1102 is laser cut. The shape memory hypotube is heat set to a "memorized" annular shape (e.g., the D-shaped operable geometry). The shape memory hypotube is superelastic such that applying sufficient stress places the plurality of segments 1102 into the compressed delivery geometry and releasing the stress allows the plurality of segments 1102 to resume the D-shaped operable geometry.

The plurality of anchors 1104 are configured to secure the segmented annuloplasty ring 1100 to the annulus of the heart valve. In certain embodiments, the anchors 1104 are sufficient such that additional suturing of the segmented annuloplasty ring 1100 to the valve annulus is not needed. In FIG. 11, the anchors 1104 are curved in the illustrated deployed configuration. Anchors in other embodiments may include other shapes, such as linear or helical deployed configurations. In certain embodiments, the anchors 1104 include a shape memory material (e.g., Nitinol) that is heat set to a deployed configuration (e.g., linear, helical, or curved configuration shown in FIG. 11). Artisans will recognize from the disclosure herein, that combinations of different deployed configurations may also be used.

The anchors 1104 are superelastic such that applying sufficient stress places the anchors 1104 into an introduction configuration and releasing the stress allows the anchors 1104 to resume their respective deployed configurations. In certain embodiments, the anchors 1104 lay flat against the plurality of segments 1102 in the introduction configuration during insertion of the ring 1100 through the catheter. As discussed below, in other embodiments, the anchors 1104 are retracted inside the segmented ring 1100 in the introduction configuration during insertion of the ring 1100 through the catheter. In such embodiments, the anchors 1104 may be selectively deployed at a desired time (e.g., after the segmented ring 1100 is properly positioned against the annulus of the heart valve). In certain embodiments, the superelastic property of the anchors 1104 is used to self-propel the anchors 1104 into the annulus of the heart valve.

The ring closure lock 1106 is used to secure the two open ends of the segmented annuloplasty ring 1100 to form a closed ring. As shown in FIG. 11, in certain embodiments, the ring closure lock 1106 includes a female snap 1110 and a male snap 1112. As discussed below, the segmented annuloplasty ring 1100 may be "snap locked" using wires or sutures to pull the male snap 1112 into the female snap 1110. In certain embodiments, a gap (e.g., between about 3 mm and 5 mm) is left between the female snap 1110 and the male snap 1112 after the anchors 1104 are deployed within the tissue of the valve annulus. Then, the two ends are snapped together to provide cinching of the valve annulus. This cinching is similar to a technique used by surgeons during open heart surgery (e.g., using sutures) to draw the valve annulus into a smaller or improved shape that reduces regurgitation of blood back through the valve.

Although not shown in FIG. 11, certain ring embodiments include a selectively adjustable member (discussed below) for changing the size and/or shape of the segmented annuloplasty ring 1100 postoperatively to compensate for changes in the size of the heart and/or the treated heart valve. Also not shown in FIG. 11, certain ring embodiments include a cover disposed about the entire circumference of the segmented ring 1100, or selected portions thereof. For example, in certain embodiments, the cover is disposed so as to enclose the plurality of segments 1102, while leaving uncovered at least portions of the ring closure lock 1106 (to permit snapping the lock together). The cover may include openings aligned with windows (discussed below) in the plurality of segments 1102 through which the plurality of anchors 1104 is deployed. In other embodiments, the plurality of anchors 1104 is configured to puncture through the cover during deployment. The cover may include a biocompatible material such as Dacron®, woven velour, polyurethane, polytetrafluoroethylene (PTFE), heparin-coated fabric, or the like. In other embodiments, the cover includes a biological material such as bovine or equine pericardium, homograft, patient graft, or cell-seeded tissue.

FIGS. 11A and 11B are schematic diagrams illustrating a shape memory hypotube 1113 cut to form a plurality of segments 1102 for use as an outer tube (also referred to herein as an "outer hollow member") of a segmented annuloplasty ring according to one embodiment. FIG. 11A is a plan view of a first side of the hypotube 1113 in which a plurality of anchor deployment windows 1114 are cut. FIG. 11B is a plan view of a second side of the hypotube 1113 that is opposite the windows 1114 shown in FIG. 11A. For illustrative purposes, FIG. 11C is a schematic diagram illustrating a cutting pattern 1116 used for laser processing the hypotube 1113 shown in FIGS. 11A and 11B. While FIGS. 11A and 11B show respective (opposite) sides of the hypotube 1113, the cutting pattern 1116 corresponds to the entire hypotube 1113 as if the hypotube were cut along an axis 1118 of the surface shown in FIG. 11A and unrolled. Thus, for example, each window 1114 shown in FIG. 11A is shown in FIG. 11C as being split between a first half of the window 1114(a) and a second half of the window 1114(b).

The hypotube 1113 includes a through hole 1120, 1121 at each end (or two perpendicular through holes at each end according to FIG. 11C) to allow one or more pins (not shown) to couple the male and female components of the ring closure lock 1106 to respective ends of the hypotube 1113. The hypotube 1113 also includes a through hole 1122 (the opening 1122 shown in FIG. 11A being represented in FIG. 11C as 1122(a) and 1122(b)). As shown in FIG. 11C, the hypotube 1113 may also include a window 1124 (passing vertically through the hypotube 1113 with respect to the views shown in FIGS. 11A and 11B) that allows one or more lines or sutures (not shown) to exit the hypotube 1113. As discussed below, the sutures are used to snap lock the ring and/or to deploy the anchors 1104.

The cutting pattern 1116 shown in FIG. 11C defines the configuration of the plurality of segments 1102 and how the segments 1102 interact with adjacent segments as the hypotube transitions from a compressed delivery geometry shown in FIGS. 1C and 1D to the annular operable geometry shown in FIG. 11. As shown in FIG. 11B, the hypotube in this example embodiment includes a "tongue and groove" pattern wherein a tongue 1126 of one segment interfaces with a groove 1128 of an adjacent segment as the inner circumference of the ring is formed. The cutting pattern 1116 provides rigidity to the hypotube 1113 in the annular operable geometry, allows the hypotube 1113 to easily transition from the compressed delivery geometry to the annular operable geometry.

Figure 12A:
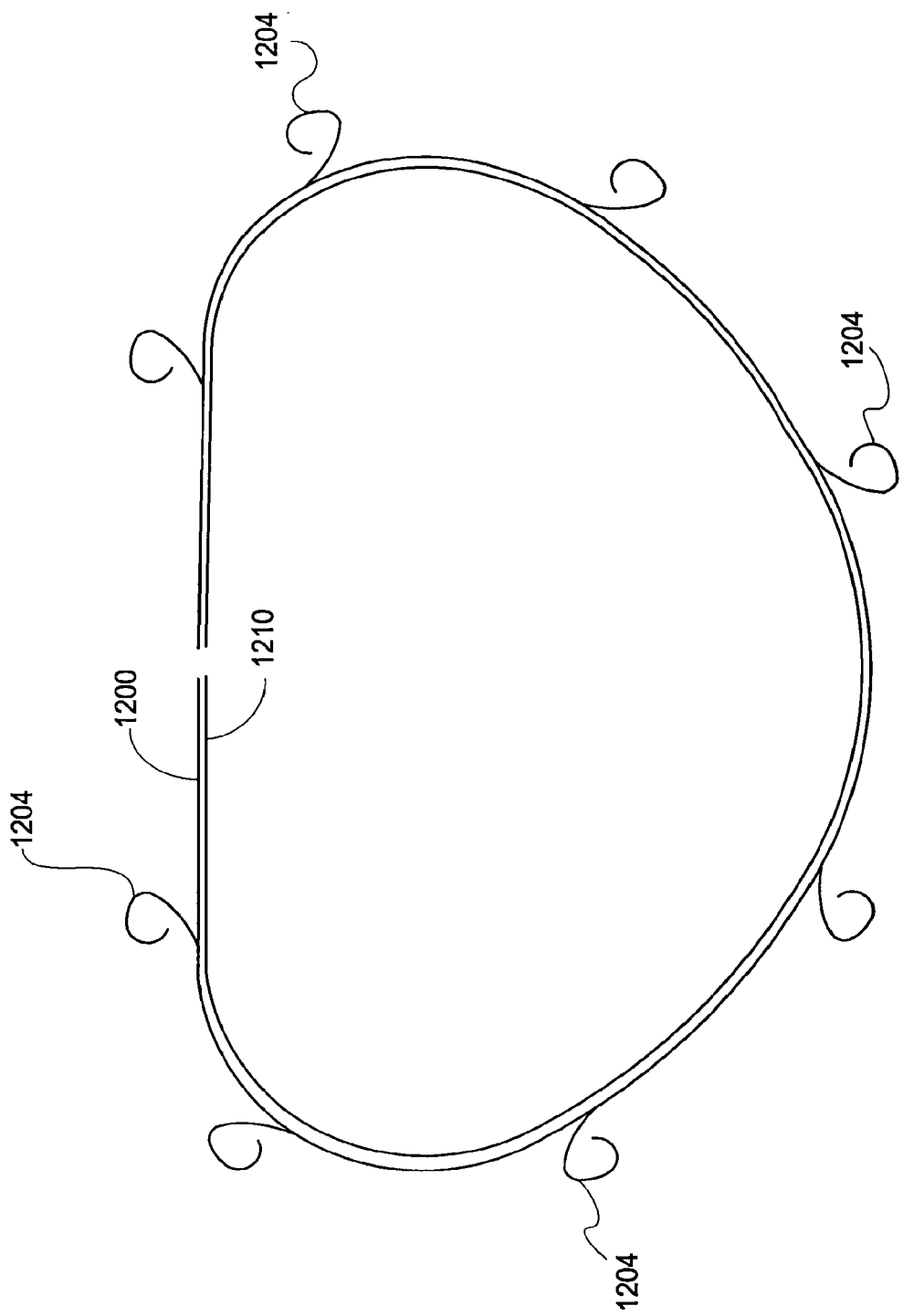
FIG. 12A is a simplified schematic diagram illustrating a side view of an internal anchor ribbon including the curved anchors shown in FIG. 11 according to one embodiment.

In certain embodiments, deployment of the anchors 1104 is accomplished using an internal anchor member that is selectively movable within the hollow tube formed by the plurality of segments 1102. For example, FIG. 12A is a simplified schematic diagram illustrating a side view of an internal anchor ribbon 1200 including the curved anchors 1104 shown in FIG. 11 according to one embodiment. The curved anchors 1104 may be affixed (e.g., laser welded) to the internal anchor ribbon 1200 or directly cut into the internal anchor ribbon 1200 (as discussed with respect to FIGS. 12B and 12C). Like the anchors 1104, the internal anchor ribbon 1104 includes a superelastic shape memory material (e.g., Nitinol) that is heat set to the same memorized annular shape as the plurality of segments 1102 (shown in FIGS. 11 and 12A as D-shaped).

The internal anchor ribbon 1200 may be slid (e.g., using wires or sutures) within the hollow tube formed by the plurality of segments 1102 of the ring 1100. To reduce friction between the internal anchor ribbon 1200 and the plurality of segments 1102, certain ring embodiments include an internal glide ribbon 1210. The internal glide ribbon 1210 may include a low-friction material (e.g., as a coating or covering) such as PTFE or other polymer. In addition, or in other embodiments, the internal glide ribbon 1210 includes a superelastic shape memory material (e.g., Nitinol) that is heat set to the same memorized annular shape as the plurality of segments 1102 (shown in FIGS. 11 and 12A as D-shaped). Thus, certain embodiments include three D-shaped superelastic members (the outer tube of segments 1102, the internal anchor ribbon 1200, and the internal glide ribbon 1210), which cooperate to increase the rigidity of the ring 1100.

Figure 12B:
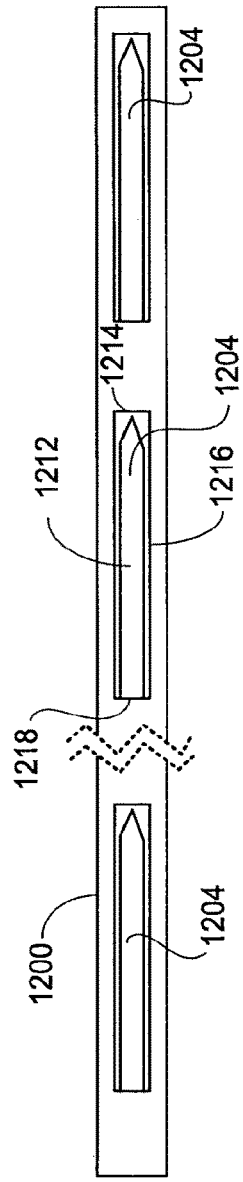
FIG. 12B is a schematic diagram illustrating a top view of the anchors cut into the internal anchor ribbon shown in FIG. 12A in an elongate geometry according to one embodiment.
Figure 12C:
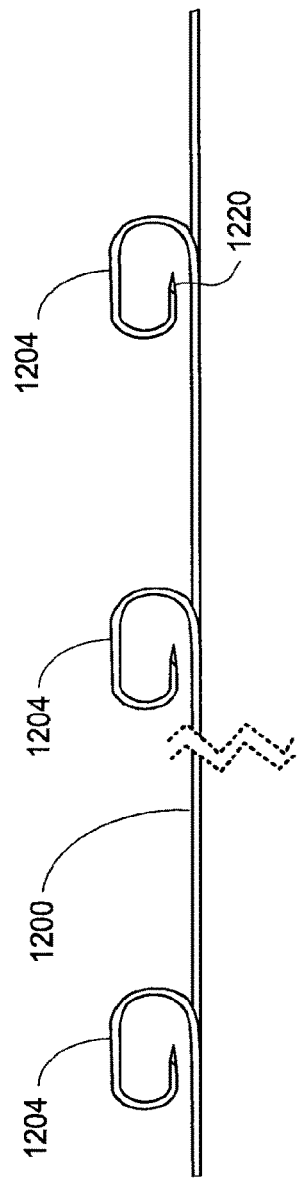
FIG. 12C is a schematic diagram illustrating a side view of the internal anchor ribbon in an elongate geometry and the anchors in a curled or curved deployed configuration according to one embodiment.
Figure 12D:
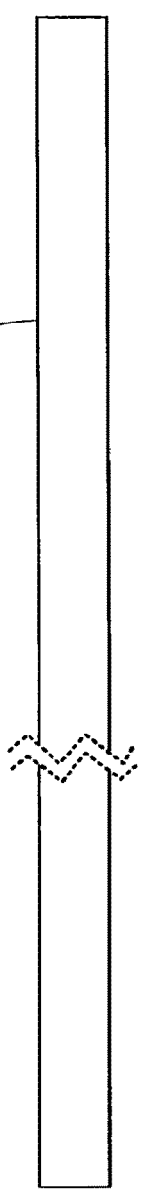
FIG. 12D is a schematic diagram illustrating a top view of an internal glide ribbon shown in FIG. 12A in an elongate geometry according to one embodiment.
Figure 12E:
FIG. 12E is a schematic diagram illustrating a side view of the internal glide ribbon shown in FIG. 12D.

FIG. 12B is a schematic diagram illustrating a top view of the anchors 1104 cut into the internal anchor ribbon 1200 shown in FIG. In this example, a laser is used to cut the anchors 1104 along a first side 1212, a second side 1214 (e.g., in a pointed or tip shape), and a third side 1216, while leaving a fourth side 1218 of the anchor 1104 uncut and attached to the internal anchor ribbon 1200. After cutting, the anchors 1104 are heat set to the desired memorized shape for the deployed configuration. For example, FIG. 12C is a schematic diagram illustrating a side view of the internal anchor ribbon 1200 and the anchors 1104 in a curled or curved deployed configuration according to one embodiment. The amount of curvature in the deployed configuration of the anchors 1104 may depend on the particular application. In the example shown in FIG. 12C, the anchors 1104 fold back on themselves such that the prong or tip 1220 points parallel to or away from the internal anchor ribbon 1200. FIG. 12D is a schematic diagram illustrating a top view of the internal glide ribbon 1210, and FIG. 12E is a schematic diagram illustrating a side view of the internal glide ribbon 1210, according to one embodiment.

FIGS. 13A and 13B are simplified schematics illustrating cross-section side views of an annuloplasty ring 1300 before (FIG. 13A) and after (FIG. 13B) deployment of the anchors 1104 shown in FIG. 12C according to one embodiment. For illustrative purposes, the ring 1300 in FIGS. 13A and 13B is shown in an elongate geometry. Artisans will recognize from the disclosure herein, however, that the anchors 1104 are generally deployed when the ring 1300 is in the annular operable geometry.

The illustrated ring 1300 includes an outer tube 1310 (e.g., formed by the plurality of segments 1102 shown in FIG. 11) including a plurality of anchor deployment windows 1312. During the manufacturing of the ring 1300, and before the ring 1300 is loaded into the catheter, the internal anchor ribbon 1200 and the internal glide ribbon 1210 are inserted into the outer tube 1310 in a position where the anchors 1104 are prevented from exiting through the windows 1312. As shown in FIG. 13A, inserting the internal anchor ribbon 1200 into the outer tube 1300 prevents the anchors from assuming their fully curved deployed configuration.

For deploying the anchors 1104, the internal anchor ribbon 1200 may include (or may be attached to) a hook or loop 1314 for engaging a wire or suture 1316 that may be pulled by a user through the catheter (e.g., in the direction of arrow 1318 in FIG. 13A) to move the tip of each anchor 1104 to a corresponding window 1312. In certain embodiments, the anchors 1104 and windows 1312 are arranged such that the tip of each anchor 1104 reaches its respective window 1312 at substantially the same time as the other anchor/window pairs. As shown in FIG. 13B, once the tips of the anchors 1104 reach the respective windows 1312, the superelasticity of the anchors 1104 propel the internal anchor ribbon 1200 in the opposite direction (as indicated by arrow 1320) as the anchors 1104 spring out the windows 1312 (as indicated by arrow 1322) to resume their curved configurations, which drives the anchors 1104 into surrounding tissue (e.g., the heart valve annulus). Thus, the superelasticity of the anchors 1104 allows the anchors 1104 to be self-propelled into the tissue adjacent or proximate to the ring 1300.

Figure 14A:
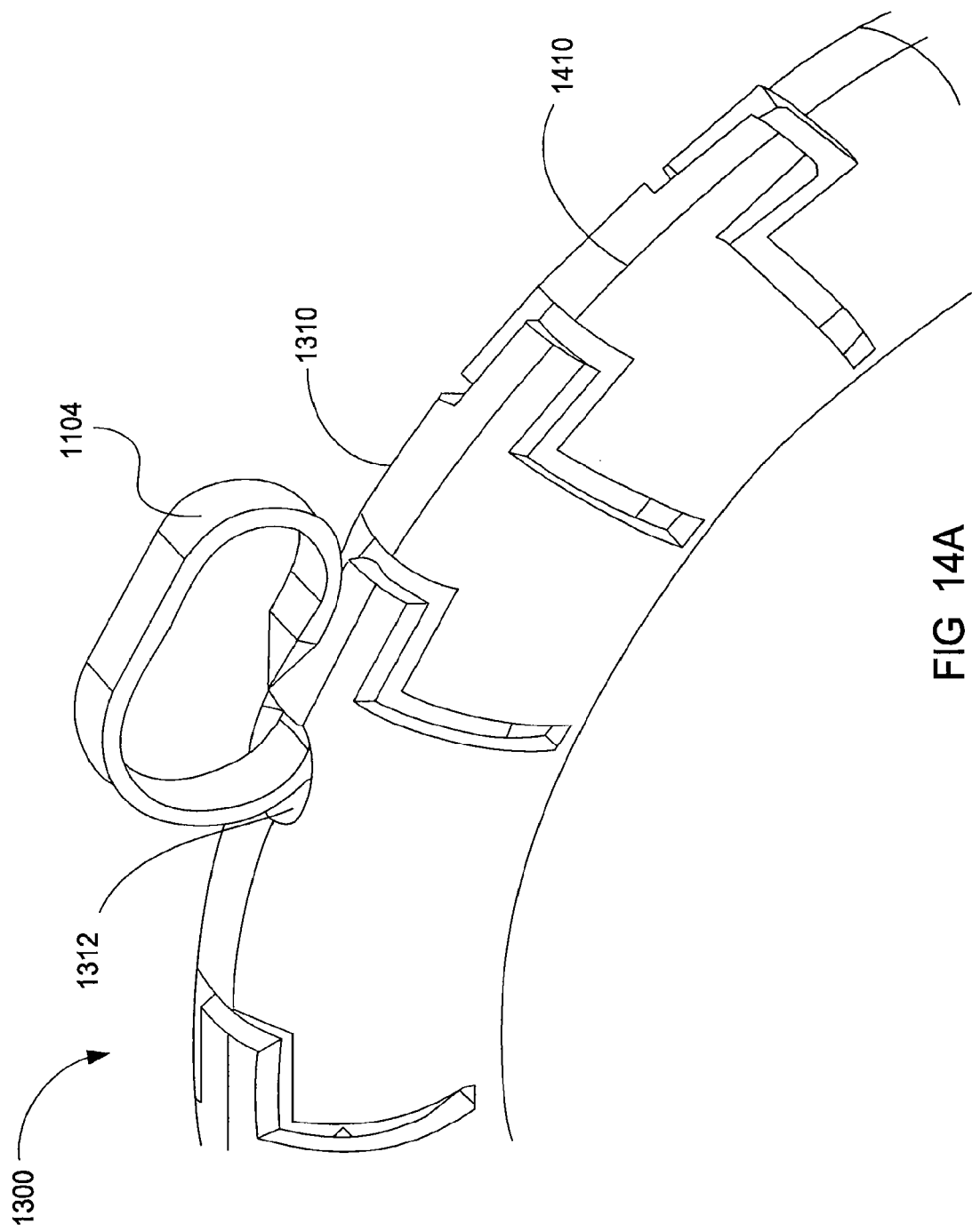
FIG. 14A is a schematic diagram illustrating a perspective view of a portion of the annuloplasty ring shown in FIGS. 13A and 13B with a deployed curved anchor according to one embodiment.
Figure 14B:
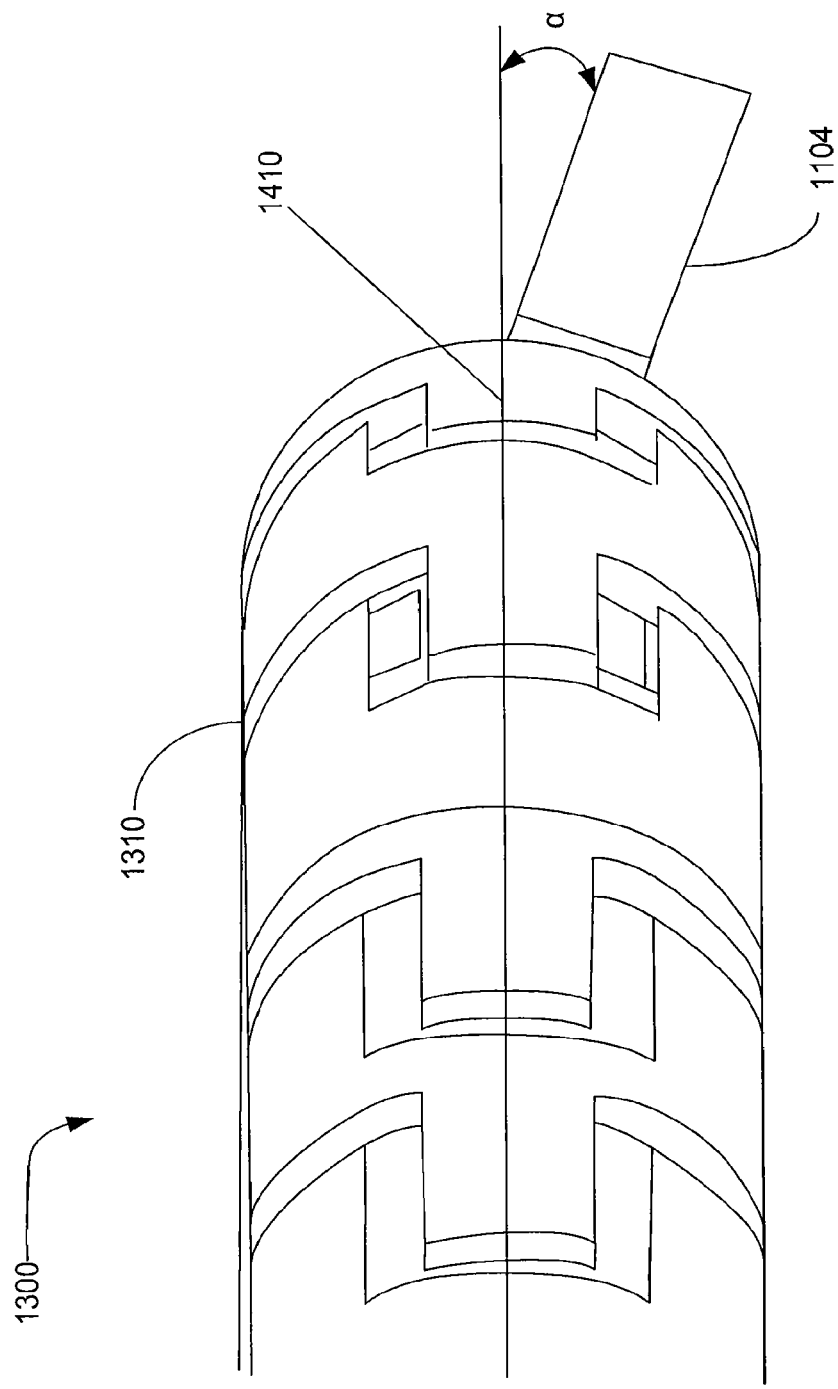
FIG. 14B is a schematic diagram illustrating a side view of a portion of the annuloplasty ring shown in FIG. 14A.

FIG. 14A is a schematic diagram illustrating a perspective view of a portion of the annuloplasty ring 1300 shown in FIGS. 13A and 13B with a deployed curved anchor 1104 according to one embodiment. FIG. 14B is a schematic diagram illustrating a side view of a portion of the annuloplasty ring shown in FIG. 14A. As shown in FIGS. 14A and 14B, the outer tube 1310 may be cut to define segments (such as the plurality of segments 1102 shown in FIG. 11). The outer tube 1310 also includes the windows 1312 (one window shown in FIG. 14A) described above and schematically represented in FIGS. 13A and 13B. As shown in FIG. 14B, in certain embodiments, the deployed anchors 1104 form an angle α (e.g., approximately 45 degrees) with a plane 1410 of the ring 1300 to provide the anchors 1104 with improved access to the valve annulus when the ring is positioned against the valve annulus. During anchor deployment, the plane 1410 of the ring 1300 is substantially parallel to the plane of the annulus of the target valve.

Figure 15:
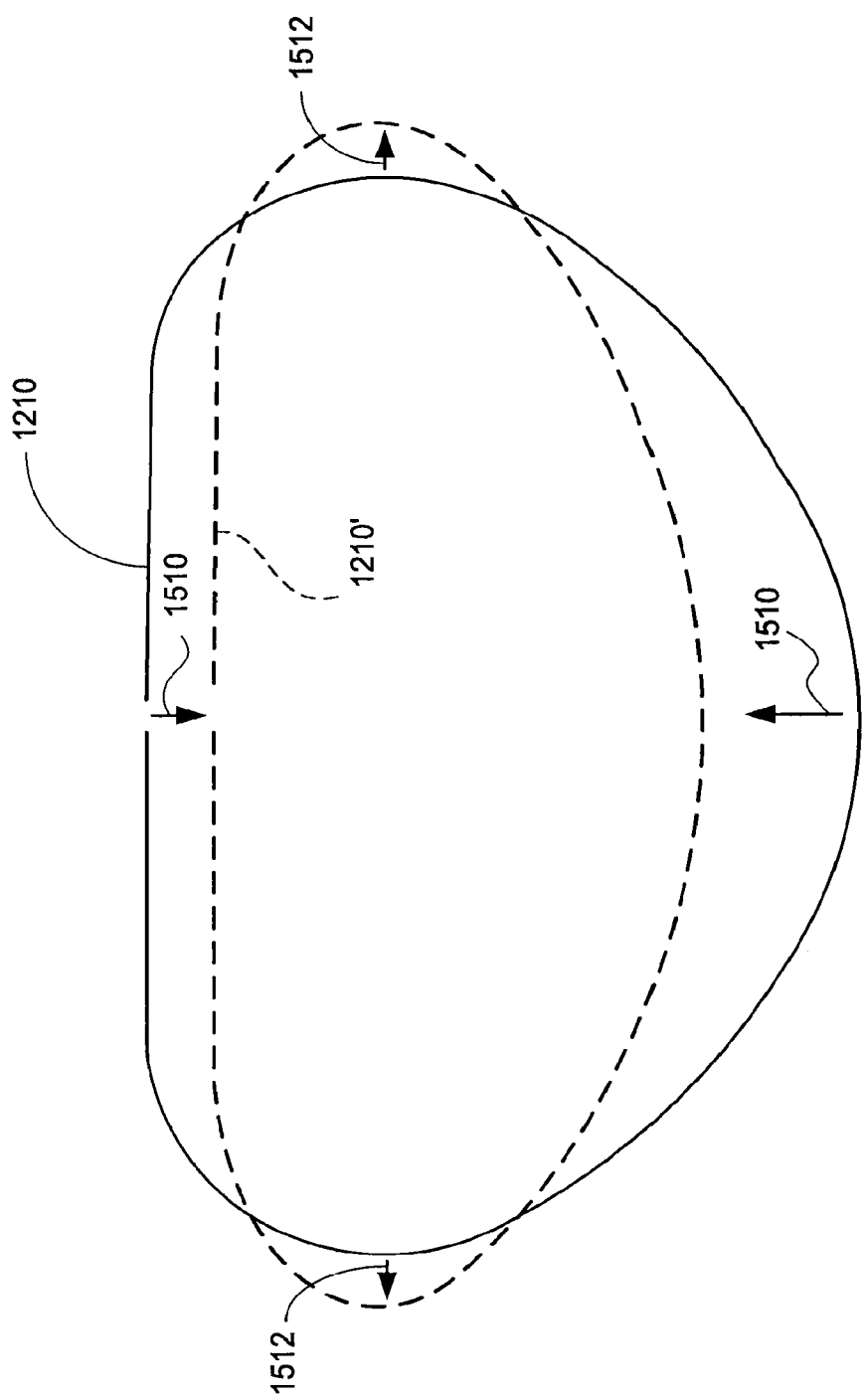
FIG. 15 is a simplified schematic diagram illustrating a side view of the internal glide ribbon shown in FIG. 12A used as a selectively adjustable member according to one embodiment.

FIG. 15 is a simplified schematic diagram illustrating a side view of the internal glide ribbon 1210 shown in FIG. 12A used as a selectively adjustable member according to one embodiment. As discussed above, certain ring embodiments include a selectively adjustable member for changing the size and/or shape of the annuloplasty ring 1100 (shown in FIG. 11) postoperatively to compensate for changes in the size of the heart and/or the treated heart valve. Thus, FIG. 15 illustrates the internal glide ribbon 1210 in the D-shaped geometry used immediately after implanting the ring, as well as an "activated" geometry or shape 1210' (shown in dashed lines) that further reduces the size of the mitral valve annulus in the (A-P) direction (as indicated by arrows 1510). Such A-P contraction improves the coaptation of the leaflets such that a gap between the leaflets sufficiently closes during left ventricular contraction. In certain embodiments, the activated shape 1210' also expands in the direction of arrows 1512 (the C-C direction) to pull leaflet commissures away from each other, which draws the leaflets closer together and further improves their coaptation. However, in certain other embodiments, the ring 1100 does not expand in the direction of the arrows 1512.

As used herein, "postoperatively" refers to a time after implanting an annuloplasty ring, such as the segmented annuloplasty ring 1100 shown in FIG. 11 or other rings described in other embodiments, and closing the body opening through which the ring 1100 was introduced into the patient's body. For example, the ring 1100 may be implanted in a child whose heart grows as the child gets older. Thus, the size of the ring 1100 may need to be increased. As another example, the size of an enlarged heart may start to return to its normal size after the ring 1100 is implanted. Thus, the size of the ring 1100 may need to be decreased postoperatively to continue to reinforce the heart valve annulus.

Thus, in certain embodiments, the ring 1100 includes a selectively adjustable member (e.g., the internal glide ribbon 1210 shown in FIGS. 12A and 15) with a shape memory material (e.g., NiTi, Alloy-B) that is responsive to changes in temperature and/or exposure to a magnetic field. The ring 1100 is adjusted in vivo by applying an energy source to activate the selectively adjustable member and cause it to change to a memorized shape. The energy source may include, for example, radio frequency (RF) energy, x-ray energy, microwave energy, ultrasonic energy such as focused ultrasound, high intensity focused ultrasound (HIFU) energy, light energy, electric field energy, magnetic field energy, combinations of the foregoing, or the like. For example, one embodiment of electromagnetic radiation that is useful is infrared energy, having a wavelength in a range between approximately 1750 nanometers and approximately 11600 nanometers. This type of infrared radiation may be produced efficiently by a solid state diode laser. In certain embodiments, the implanted ring 1100 is selectively heated using short pulses of energy having an on and off period between each cycle. The energy pulses provide segmental heating that allows segmental adjustment of portions of the annuloplasty ring without adjusting the entire implant.

In certain embodiments, the ring 1100 includes an energy absorbing material to increase heating efficiency and localize heating in the area of the selectively adjustable member. Thus, damage to the surrounding tissue is reduced or minimized. Energy absorbing materials for light or laser activation energy may include nanoshells, nanospheres and the like, particularly where infrared laser energy is used to energize the material. Such nanoparticles may be made from a dielectric, such as silica, coated with an ultra thin layer of a conductor, such as gold, and be selectively tuned to absorb a particular frequency of electromagnetic radiation. In certain such embodiments, the nanoparticles range in size between about 15 nanometers and about 120 nanometers and can be suspended in a suitable material or solution, such as saline solution. Coatings comprising nanotubes or nanoparticles can also be used to absorb energy from, for example, HIFU, MIll, inductive heating, or the like.

In other embodiments, thin film deposition or other coating techniques such as sputtering, reactive sputtering, metal ion implantation, physical vapor deposition, and chemical deposition can be used to cover portions or all of the selectively adjustable member. Such coatings can be either solid or microporous. When HIFU energy is used, for example, a microporous structure traps and directs the HIFU energy toward the shape memory material. The coating improves thermal conduction and heat removal. In certain embodiments, the coating also enhances radio-opacity of the annuloplasty ring implant. Coating materials can be selected from various groups of biocompatible organic or non-organic, metallic or non-metallic materials such as Titanium Nitride (TiN), Iridium Oxide (Irox), Carbon, Platinum black, Titanium Carbide (TiC) and other materials used for pacemaker electrodes or implantable pacemaker leads. Other materials discussed herein or known in the art can also be used to absorb energy.

In addition, or in other embodiments, fine conductive wires such as platinum coated copper, titanium, tantalum, stainless steel, gold, or the like, are wrapped around the selectively adjustable member to allow focused and rapid heating of the selectively adjustable member while reducing undesired heating of surrounding ring 1100 and/or tissues. In certain such embodiments, the electrically conductive wires are electrically insulated from other components of the ring 1100, such as the shape memory material used in the plurality of segments 1102 and/or the plurality of anchors 1104.

The energy source for activating the shape memory material of the selectively adjustable member may be surgically applied after the ring 1100 has been implanted by percutaneously inserting a catheter into the patient's body and applying the energy through the catheter. For example, RF energy, light energy, or thermal energy (e.g., from a heating element using resistance heating) can be transferred to the selectively adjustable member through a catheter positioned on or near the selectively adjustable member. Alternatively, thermal energy can be provided to the shape memory material by injecting a heated fluid through a catheter or circulating the heated fluid in a balloon through the catheter placed in close proximity to the selectively adjustable member. As another example, the shape memory material in the selectively adjustable member can be coated with a photodynamic absorbing material that is activated to heat the selectively adjustable member when illuminated by light from a laser diode or directed to the coating through fiber optic elements in a catheter. In certain such embodiments, the photodynamic absorbing material includes one or more drugs that are released when illuminated by the laser light. In certain embodiments, a subcutaneous electrode or coil couples energy from a dedicated activation unit. In certain such embodiments, the subcutaneous electrode provides telemetry and power transmission between the system and the annuloplasty ring. The subcutaneous electrode allows more efficient coupling of energy to the implant with minimum or reduced power loss. In certain embodiments, the subcutaneous energy is delivered to the selectively adjustable member via inductive coupling.

In other embodiments, the energy source is applied in a non-invasive manner from outside the patient's body. In certain such embodiments, the external energy source is focused to provide directional heating to the shape memory material of the selectively adjustable member so as to reduce or minimize damage to the surrounding tissue. For example, in certain embodiments, a handheld or portable device including an electrically conductive coil generates an electromagnetic field that non-invasively penetrates the patient's body and induces a current in the selectively adjustable member. The current heats the selectively adjustable member and causes the shape memory material therein to transform to a memorized shape. In certain such embodiments, the selectively adjustable member also includes an electrically conductive coil wrapped around or embedded in the memory shape material. The externally generated electromagnetic field induces a current in the selectively adjustable member's coil, causing it to heat and transfer thermal energy to the shape memory material therein.

Figure 15A:
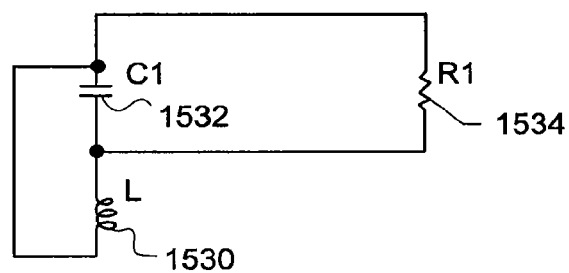
FIGS. 15A, 15B, and 15C are schematic diagrams of circuitry for using RF induction to activate the shape memory material of the internal glide ribbon according to one embodiment.
Figure 15B:
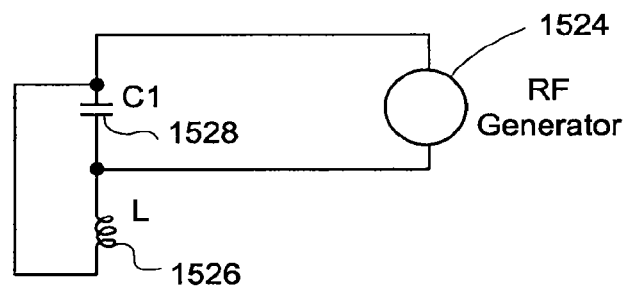
Figure 15C:
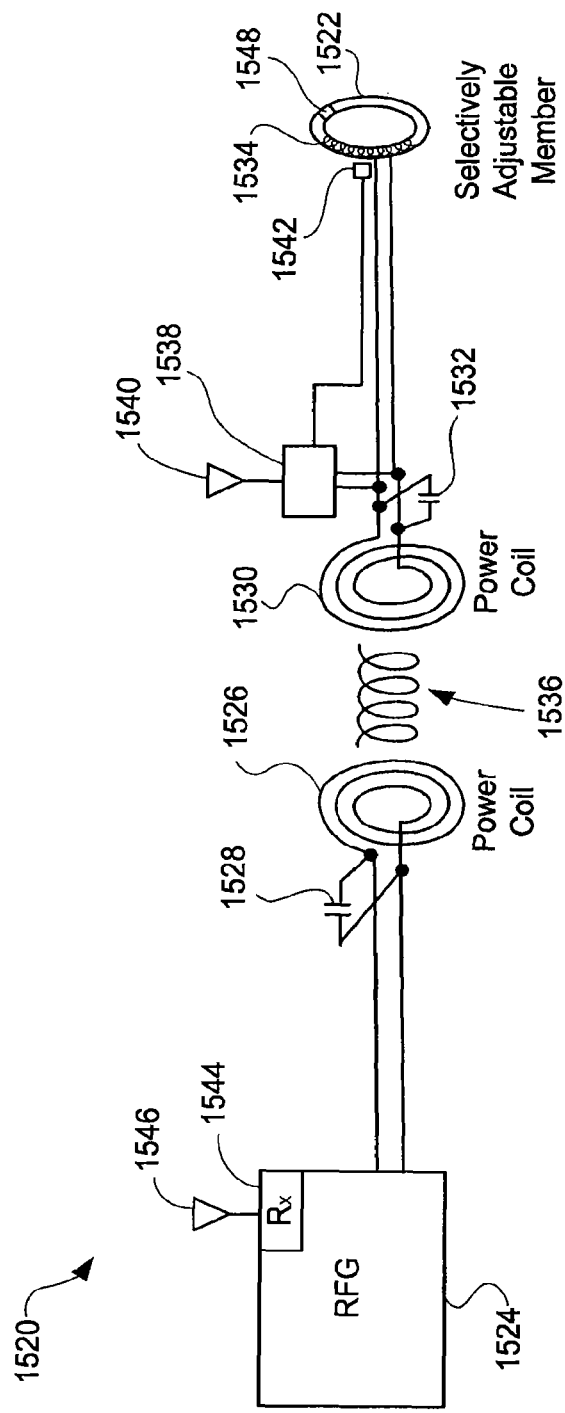

By way of example, FIGS. 15A, 15B, and 15C are schematic diagrams of circuitry for using RF induction to activate the shape memory material of the internal glide ribbon 1210 according to one embodiment. FIG. 15A illustrates circuitry located in a selectively adjustable annuloplasty ring and FIG. 15B illustrates circuitry of an external (i.e., external to the patient) RF induction activation system according to one embodiment. FIG. 15C is a block diagram of a system 1520 for inductively activating a selectively adjustable member 1522 (e.g., the internal glide ribbon 1210) of a ring according to certain embodiments.

Referring to FIGS. 15A, 15B, and 15C, the RF induction activation system 1520 includes a power source 1524 (also referred to herein as an RF generator or RFG) capable of creating an alternating electrical signal of suitable power. The power source 1524 is connected to a delivery coil 1526 tuned to resonate at the same frequency as the output of the power source 1524. A capacitor 1528 is used to tune the delivery coil 1526 to resonate at the desired frequency. The implantable dynamically adjustable annuloplasty ring assembly includes a second (receiving) coil 1530 positioned within the patient that is designed to resonate at substantially the same frequency as that of the delivery coil 1526 connected to the power source 1524. A capacitor 1532 is used to tune the receiving coil 1530 to resonate at the desired frequency. The receiving coil 1530 is connected to a heating element 1534 (represented by a resistance R1 in FIG. 15A) wrapped around the selectively adjustable member 1522 (as shown in FIG. 15C). To activate the annuloplasty ring, the delivery coil 1526 is placed near the receiving coil 1530 of the selectively adjustable member 1522 (e.g., near the patient's chest) and switched on. Power from the resonating magnetic field 1536 (shown in FIG. 15C) is then inductively transferred across the skin barrier to the receiving coil 1530 and converted to electrical current that is subsequently used to heat the selectively adjustable member 1522. In an example embodiment, the inductance frequency is above about 1100 kHz so that any leakage current that may come in contact with the patient would not cause uncomfortable sensations during activation.

In certain embodiments, embedded computing and/or remote temperature sensing is used. For example, FIG. 15C shows that additional circuitry 1538 may be implanted in the patient. The additional circuitry 1538 may include transmitter circuitry (including an antenna 1540), a microprocessor, power circuitry, and temperature measuring circuitry (e.g., one or more thermocouple (TC) devices 1542, coupled to the additional circuitry 1538). Similarly, the RFG 1524 may include receiver circuitry 1544 (including an antenna 1546) for receiving temperature and other data from the additional circuitry 1538 implanted in the patient. Although not shown, the RFG 1524 may also include a processor for processing and displaying the information received from the additional circuitry 1538 implanted within the patient.

The information received from the additional circuitry 1538 may include, for example, the power induced in the selectively adjustable member 1522. In one embodiment, the power transferred to the selectively adjustable member 1522 is measured by reading the voltage across the selectively adjustable member 1522 and/or heating element 1534 and, because the resistance of the selectively adjustable member 1522 and/or heating element 1534 is known, the power can be calculated and communicated to the RFG 1524 by the telemetry link. In another example, the temperature and size of the selectively adjustable member 1522 may be sensed and sent by transmitter circuitry in the additional circuitry 1538 to the receiving circuitry 1544 via radiotelemetry. Temperature may be sensed using the thermocouple device 1542, and the size of the ring may be deduced via built in strain gauges 1548 (e.g., different resistance values equal a proportional change in size).

In one embodiment, the RFG 1524 automatically finds a resonant point. The RFG 1524 may be programmed to analyze wattage delivered during operation (e.g., as discussed above) and may adjust the output frequency to increase or maximize the greatest power transfer. This may be accomplished in certain embodiments by directly monitoring the current output on the delivery coil 1526, or the peak voltage induced in the receiving coil 1530 via telemetry.

In one embodiment, the system 1520 is capable of multiple resonant frequencies. For example, the heating element 1534 (coupled to the selectively adjustable member 1522) may be electrically connected to more than one coil—each coil having a different natural resonance. In another embodiment, different coils may be attached to different heating elements or devices in the ring that can be operated separately. The transmitting power source 1524 may have a set of coils (e.g., including the delivery coil 1526) that can be selectively used to couple to its respective sister coil (e.g., including the receiving coil 1530) coupled to the selectively adjustable member 1522.

By using this wireless technique of power transmission, the patient may be electrically isolated from the system 1520 during activation of an implanted device. Thus, the possibility of electrocution due to a ground fault is eliminated and/or reduced.

In some embodiments, centering of coils is used. Such embodiments use techniques of aligning the coils, such as through the use of physical landmarks molded into a housing of the implanted receiving coil, magnets, and/or infrared lighting. For example, an infrared light emitting diode (LED) may be installed on the implanted receiving coil 1530 and may light during activation. An infrared detector located on the delivery coil 1526 may be configured to give a user feedback on how much light it receives. A set of magnets may also be strategically placed in the delivery coil 1526 and receiving coil 1530. As the magnets are brought close together, the magnetic attraction may be utilized to align the coils 1526, 1530.

Example Ring Embodiments with Linear Anchors

Figure 16A:
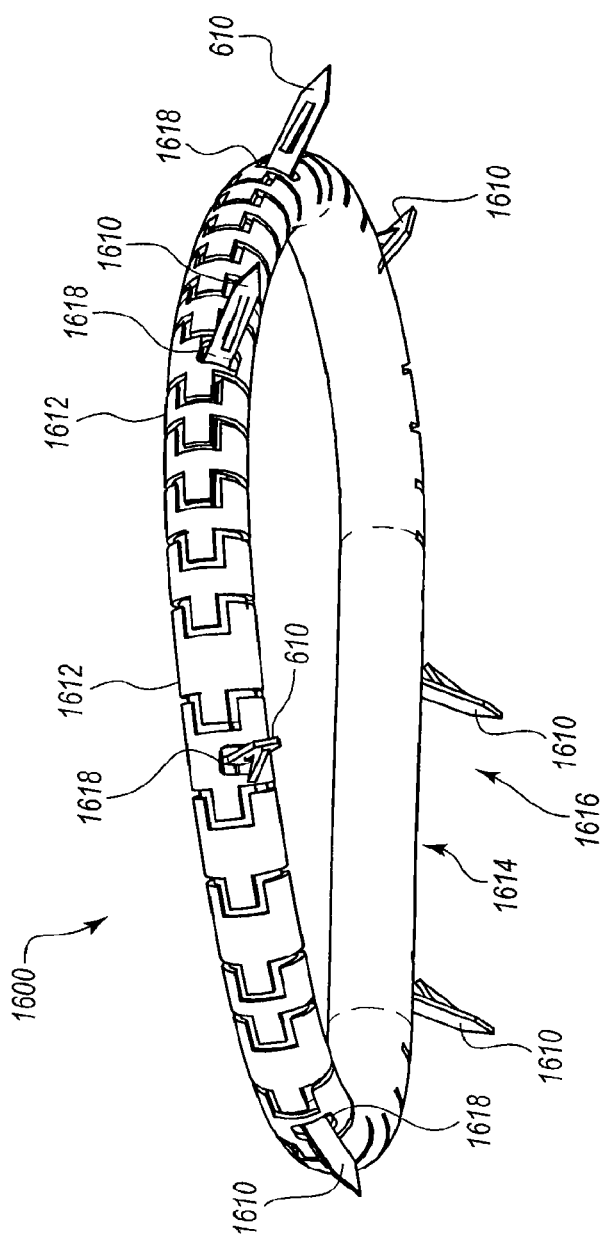
FIG. 16A is a schematic diagram illustrating a perspective view of a segmented annuloplasty ring including a plurality of linear anchors according to one embodiment.

FIG. 16A is a schematic diagram illustrating a perspective view of a segmented annuloplasty ring 1600 including a plurality of linear anchors 1610 according to one embodiment. Seven linear anchors 1610 are shown. However, artisans will understand from the disclosure herein that more linear anchors 1610 or fewer linear anchors may be used. For example, certain embodiments may use ten or more linear anchors 1610.

The segmented annuloplasty ring 1600 includes a plurality of segments 1612 at least partially cut into a shape memory hypotube that forms a "D-shape" in the annular operable geometry (e.g., when implanted around the annulus) and may be compressed into a compressed delivery geometry for implanting the ring 1600 within a patient's heart through a catheter. As discussed above with respect to FIG. 11, the ring 1600 may also include a ring closure lock 1614 (shown in a connected or locked position) for snap locking the two ends of the ring together.

As discussed above with respect to other embodiments, the ring 1600 includes a plurality of anchor deployment windows 1618 cut into the shape memory hypotube. The plurality of linear anchors 1610 may be selectively deployed through the windows 1618 in a manner similar to that described above for curved anchors 1104.

Figure 16B:
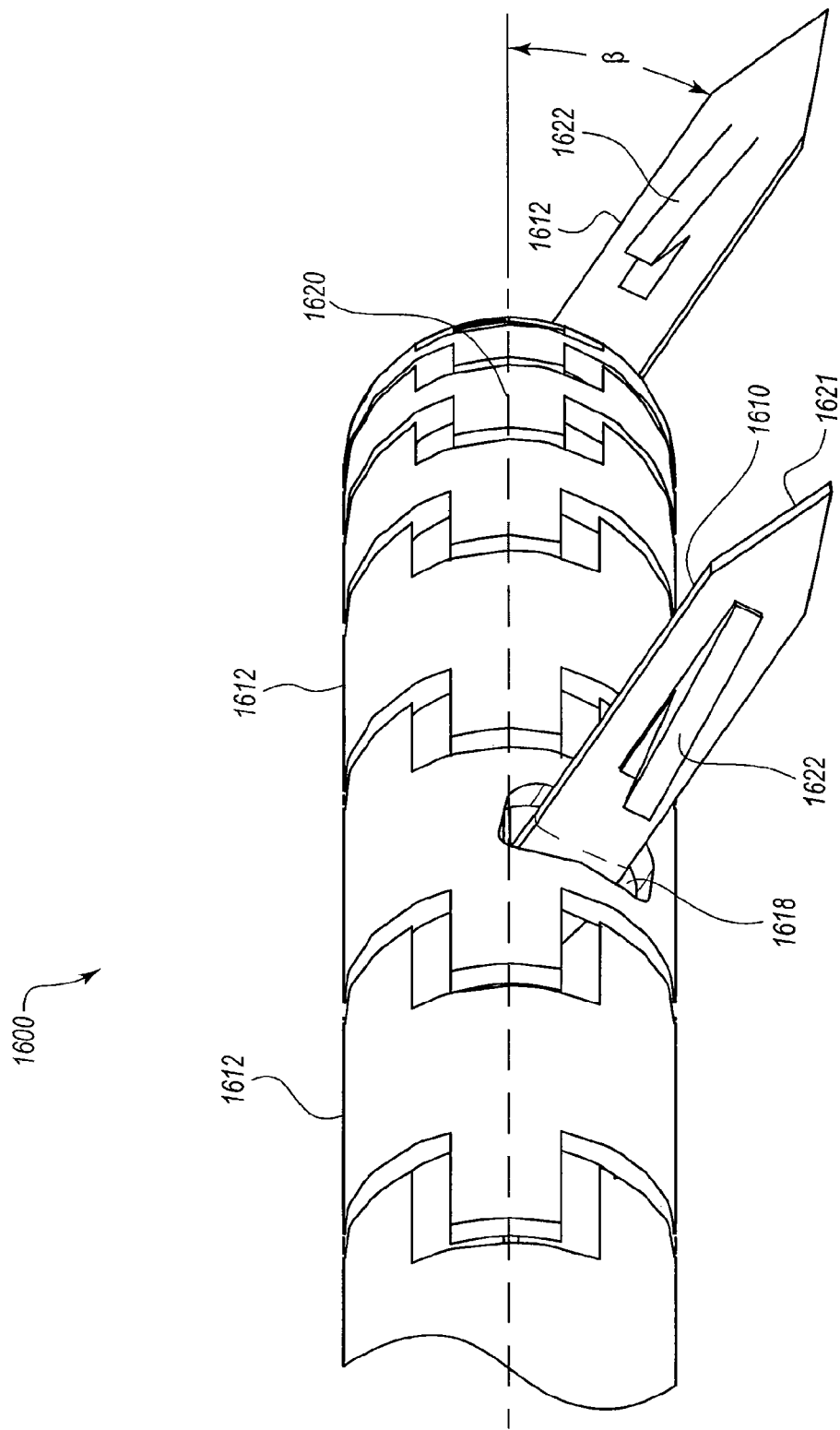
FIG. 16B is a schematic diagram illustrating a side view of a portion of the annuloplasty ring shown in FIG. 16A.

FIG. 16B is a schematic diagram illustrating a side view of a portion of the annuloplasty ring shown in FIG. 16A. As shown in FIG. 16B, in certain embodiments, the deployed linear anchors 1610 form an angle β (e.g., about 145 degrees) with a plane 1620 of the ring 1600 to provide the linear anchors 1610 with improved access to the valve annulus when the ring is positioned against the valve annulus. During anchor deployment, the plane 1620 of the ring 1600 is substantially parallel to the plane of the valve annulus. As shown in FIG. 16B, the linear anchors 1610 may include a pointed prong 1621 for penetrating tissue and a barb 1622 that secures the anchor to the tissue.

Figure 17:
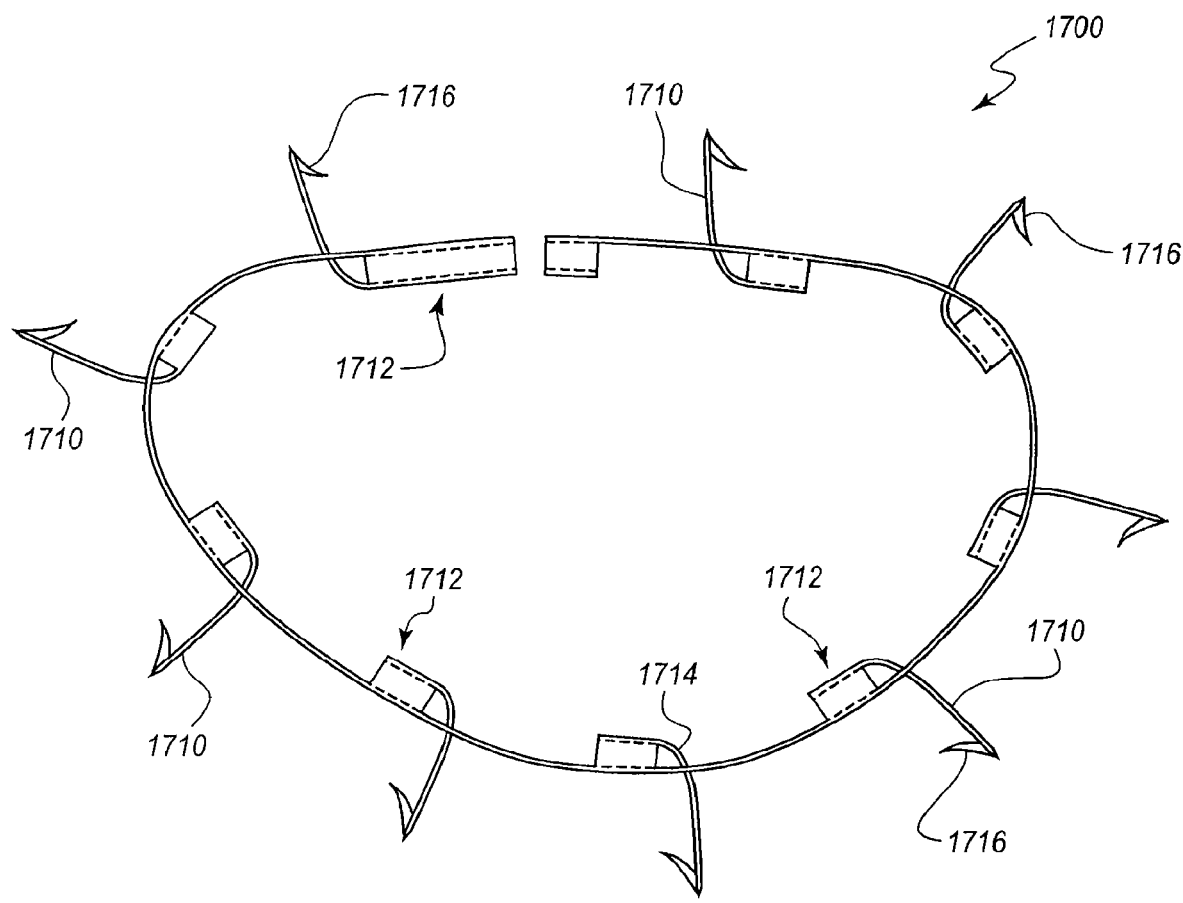
FIG. 17 is a simplified schematic diagram illustrating a side view of an internal anchor member including linear anchors according to one embodiment.

FIG. 17 is a simplified schematic diagram illustrating a side view of an internal anchor member 1700 including linear anchors 1710 according to one embodiment. The linear anchors 1710 may be affixed (e.g., laser welded) to the internal anchor member 1700. In the embodiment shown in FIG. 17, however, the internal anchor member 1700 and linear anchors 1710 are cut from a single superelastic shape memory (e.g., Nitinol) hypotube. FIG. 17, for example, shows remaining tubular portions 1712 after the hypotube is cut to form prongs 1714 of the linear anchors 1710. The remaining tubular portions 1712 facilitate sliding (e.g., using wires or sutures accessible through the catheter) the internal anchor member 1700 coaxially within the hollow tube of the ring (e.g., within the segmented annuloplasty ring 1600 shown in FIG. 16).

The internal anchor member 1700 is heat set to the same memorized annular shape as the ring. The anchors prongs 1714 can be heat set to protrude outward through windows cut in the segmented annuloplasty ring 1600. Barbs 1716 may be laser welded to the prongs 1714 to form the linear anchors 1710. The linear anchors 1710 are retracted/deployed by sliding the internal anchor member 1700 within the segmented annuloplasty ring 1600.

Figure 18A:
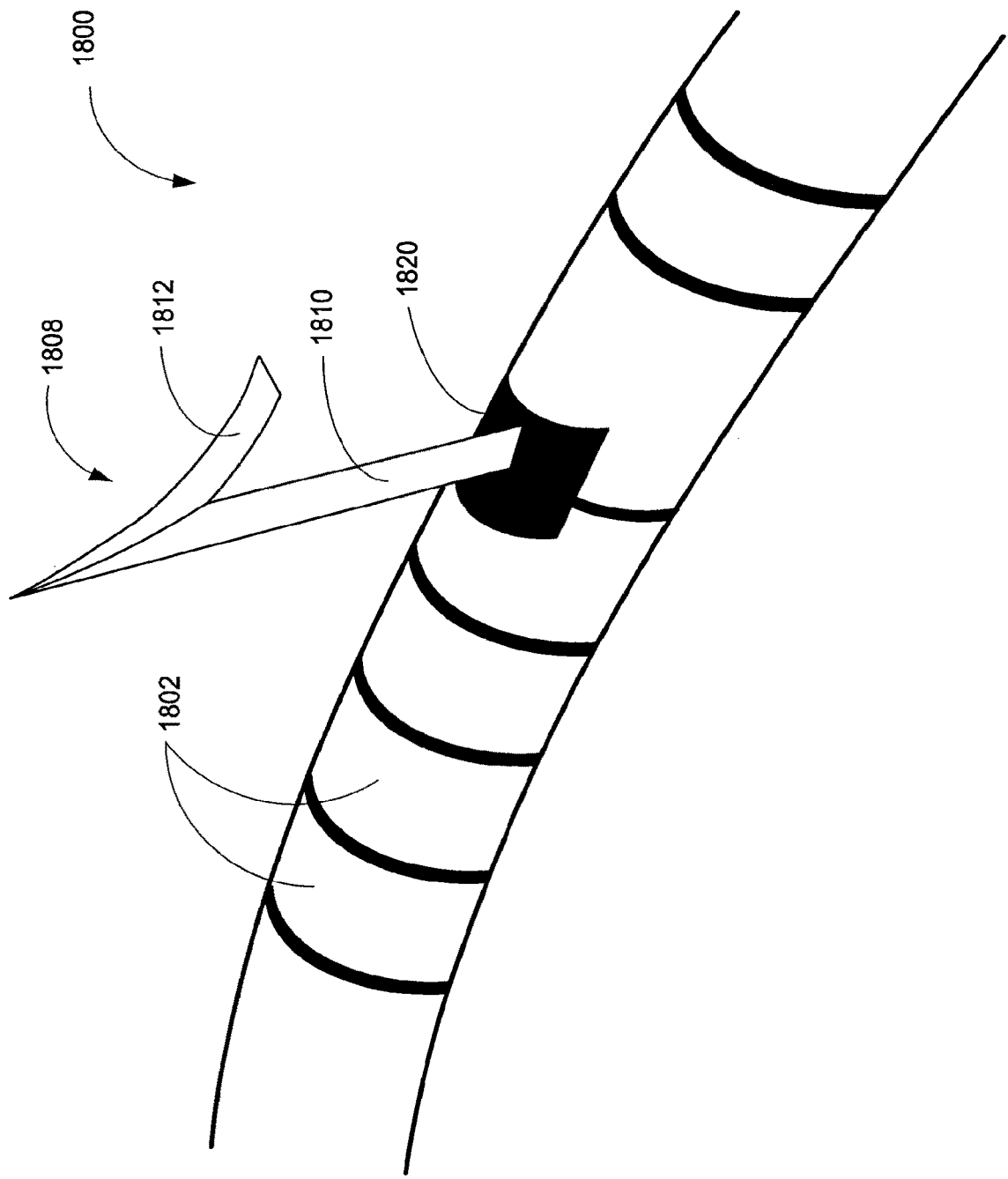
FIG. 18A is a schematic diagram illustrating an enlarged perspective view of a single-barbed anchor of a percutaneous transcatheter annuloplasty ring in an affixation configuration according to one embodiment.

FIG. 18A is a schematic diagram illustrating an enlarged perspective view of a single-barbed anchor 1808 of a percutaneous transcatheter annuloplasty ring 1800 in an affixation configuration according to one embodiment. The anchor 1808 includes a prong 1810 and a single barb 1812 welded to the prong 1810. The prong 1810 is integrated with or connected to an inner tube member (not shown, but see FIG. 17) and protrudes through a window 1820 cut in an outer tube member formed by a plurality of segments 1802.

Figure 18B:
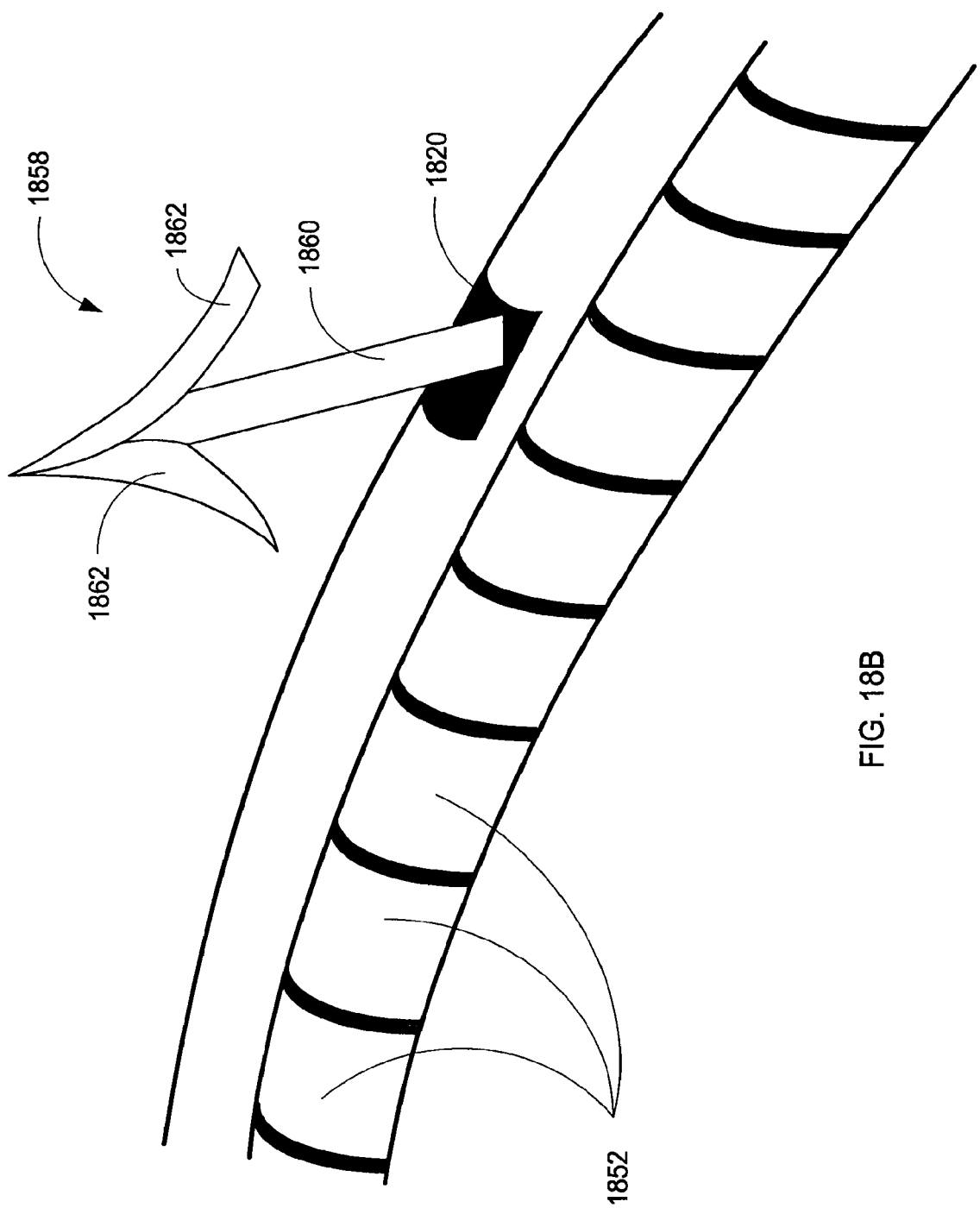
FIG. 18B is a schematic diagram of an enlarged perspective view of a dual-barbed anchor of a percutaneous transcatheter annuloplasty ring in an affixation configuration according to one embodiment.

FIG. 18B is a schematic diagram of an enlarged perspective view of a dual-barbed anchor 1858 of a percutaneous transcatheter annuloplasty ring in an affixation configuration according to one embodiment. The anchor 1858 includes a prong 1860 and two barbs 1862 welded to the prong 1860. The prong 1860 is integrated with or connected to an inner tube member (not shown) and protrudes through a window 1820 cut in an outer tube member formed by a plurality of segments 1852.

Figure 19:
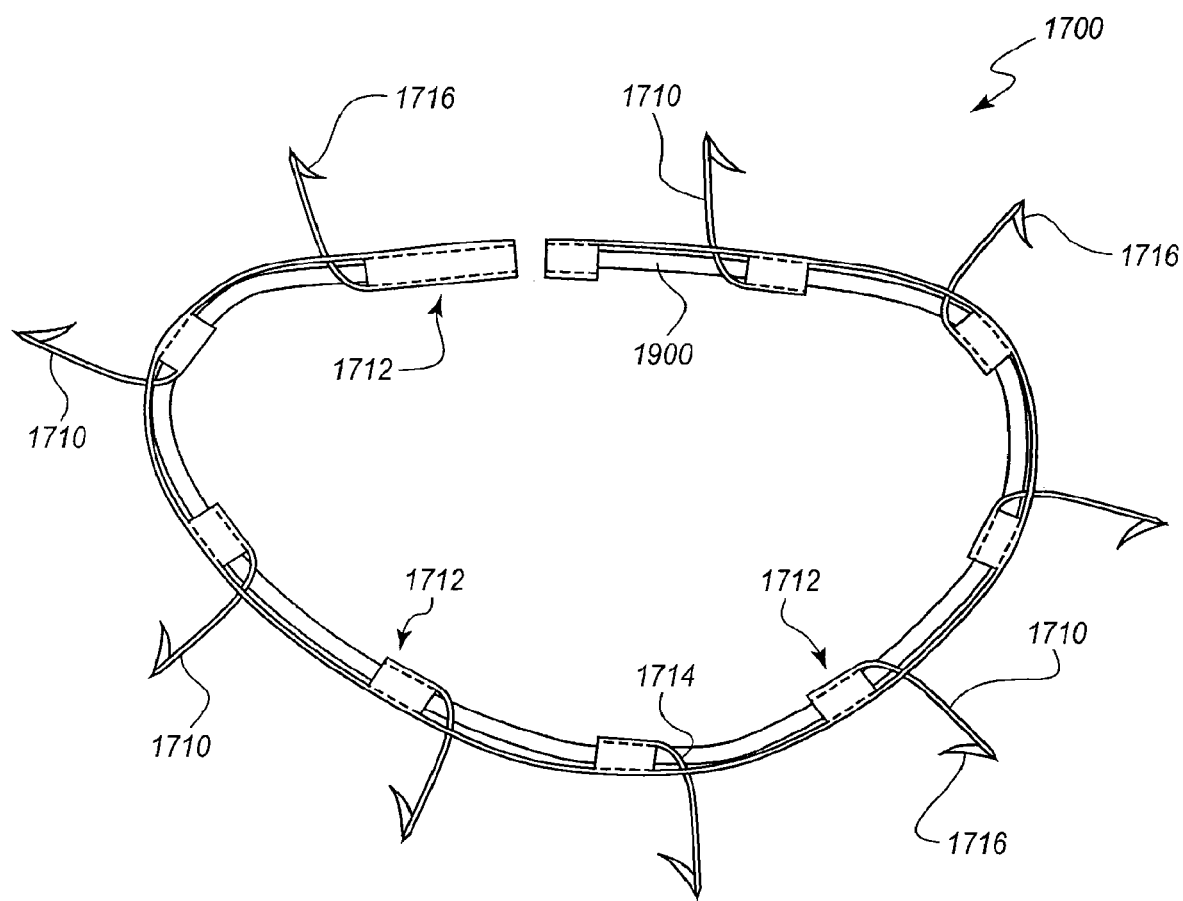
FIG. 19 is a simplified schematic diagram illustrating a side view of the internal anchor member shown in FIG. 17 and a selectively adjustable member according to one embodiment.

FIG. 19 is a simplified schematic diagram illustrating a side view of the internal anchor member 1700 shown in FIG. 17 and a selectively adjustable member 1900 according to one embodiment. As discussed above, the selectively adjustable member 1900 is configured to change the size and/or shape of the annuloplasty ring 1600 postoperatively to compensate for changes in the size of the heart and/or the treated heart valve. In FIG. 19, the selectively adjustable member 1900 is shown passing through the remaining tubular portions 1712 of the cut hypotube of the internal anchor member 1700. In such embodiments, the selectively adjustable member 1900 may be rod shaped and may have an outer diameter of about 140 microns. In other embodiments, the selectively adjustable member 1900 may be located adjacent to the internal anchor member 1700 (e.g., around the external circumference, the internal circumference, or lateral to the internal anchor member 1700).

The selectively adjustable member 1900 includes a shape memory material (e.g., NiTi Alloy-B) that is responsive to changes in temperature and/or exposure to a magnetic field. The selectively adjustable member 1900 may be activated, for example, using any of the energy sources or methods described above with respect to FIGS. 15, 15A, 15B, and 15C. The activated geometry of the selectively adjustable member 1900, according to certain embodiments, reduces the size of the mitral valve annulus in the AP direction.

Figure 20:
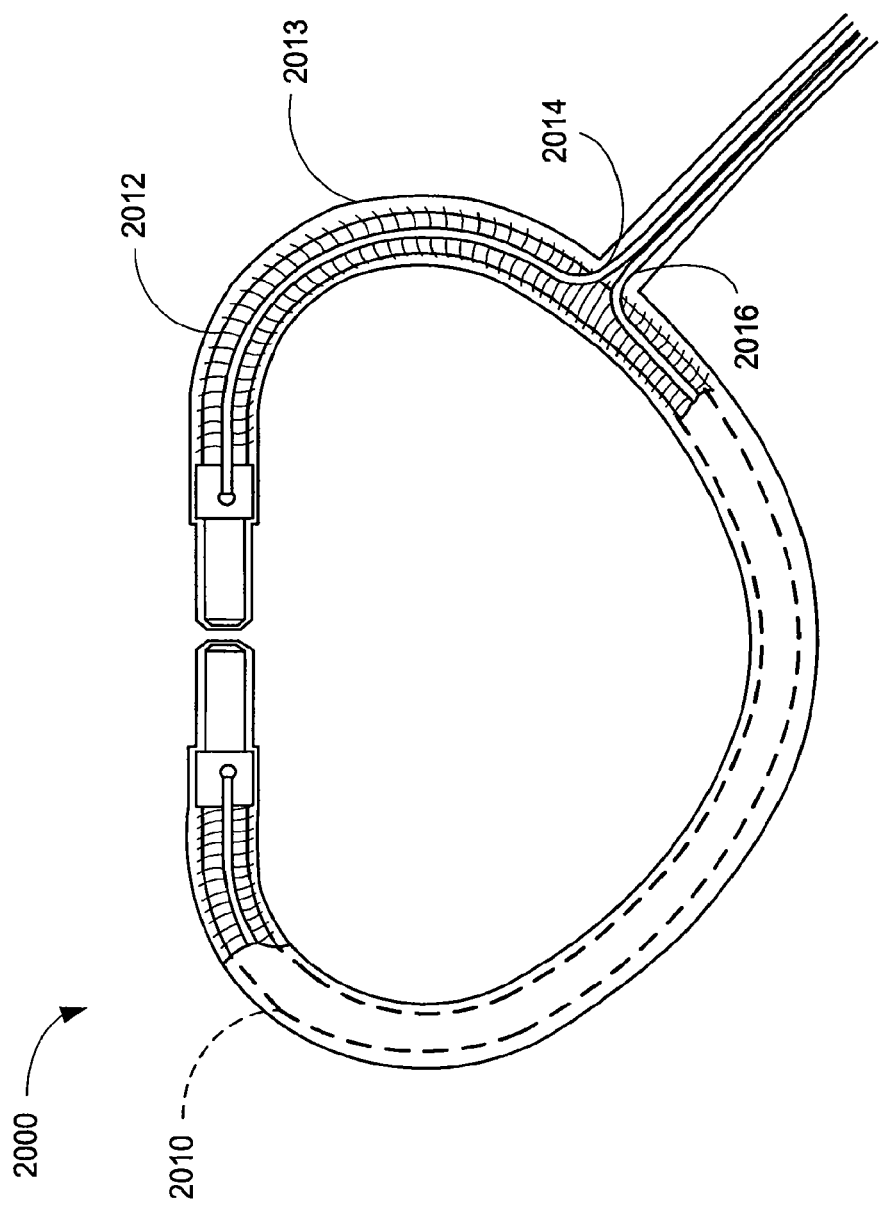
FIG. 20 is a schematic diagram illustrating a partial cross-sectional view of the selectively adjustable member shown in FIG. 19 according to one embodiment.

FIG. 20 is a schematic diagram illustrating a partial cross-sectional view of the selectively adjustable member 1900 shown in FIG. 19 according to one embodiment. The selectively adjustable member 1900 in this example includes a shape memory rod 2010, a heating element 2012 (e.g., electrically conductive wire) coiled around the shape memory rod 2010, and an electrically insulating cover 2013 surrounding the shape memory rod 2010 and heating element 2012. The electrically insulating cover 2013 prevents current passing through the heating element 2012 from flowing to nearby metals or other shape memory alloys in the ring (e.g., the outer segmented annuloplasty ring 1600 and/or the internal anchor member 1700), or to surrounding tissue. The electrically insulating cover 2013 may also provide thermal insulation to protect the surrounding tissue from excessive heat.

As shown in FIG. 20, the selectively adjustable member 1900 may include leads 2014, 2016 for providing induced current through the heating element 2012. The leads 2014, 2016 may exit through the septal wall, the right atrium subclavian vein, or both leads may follow the ring contour and exit at $P_1/P_2$ leaflet junction or $P_3/P_2$ leaflet junction.

In certain embodiments, the receiving coil 1530 (shown in FIGS. 15A and 15C) and any associated internal circuitry may be placed anywhere within the patient and outside the heart of the patient. For example, the receiving coil 1530 and/or additional circuitry 1538 may be implanted immediately below the surface of the skin and coupled to the heating element 2012 (coupled to the selectively adjustable member 1900) via one or more wires extending into the heart. In another embodiment, the receiving coil 1530 and associated internal circuitry may be integrated with the annuloplasty ring and/or the selectively adjustable member 1900. For example, the receiving coil 1530 and additional circuitry 1538 may be incorporated internal to the annuloplasty ring. In still another embodiment, the receiving coil 1530 may be implanted adjacent the lead wire and/or the receiving coil, in close proximity to the selectively adjustable member 1900.

Figure 21A:
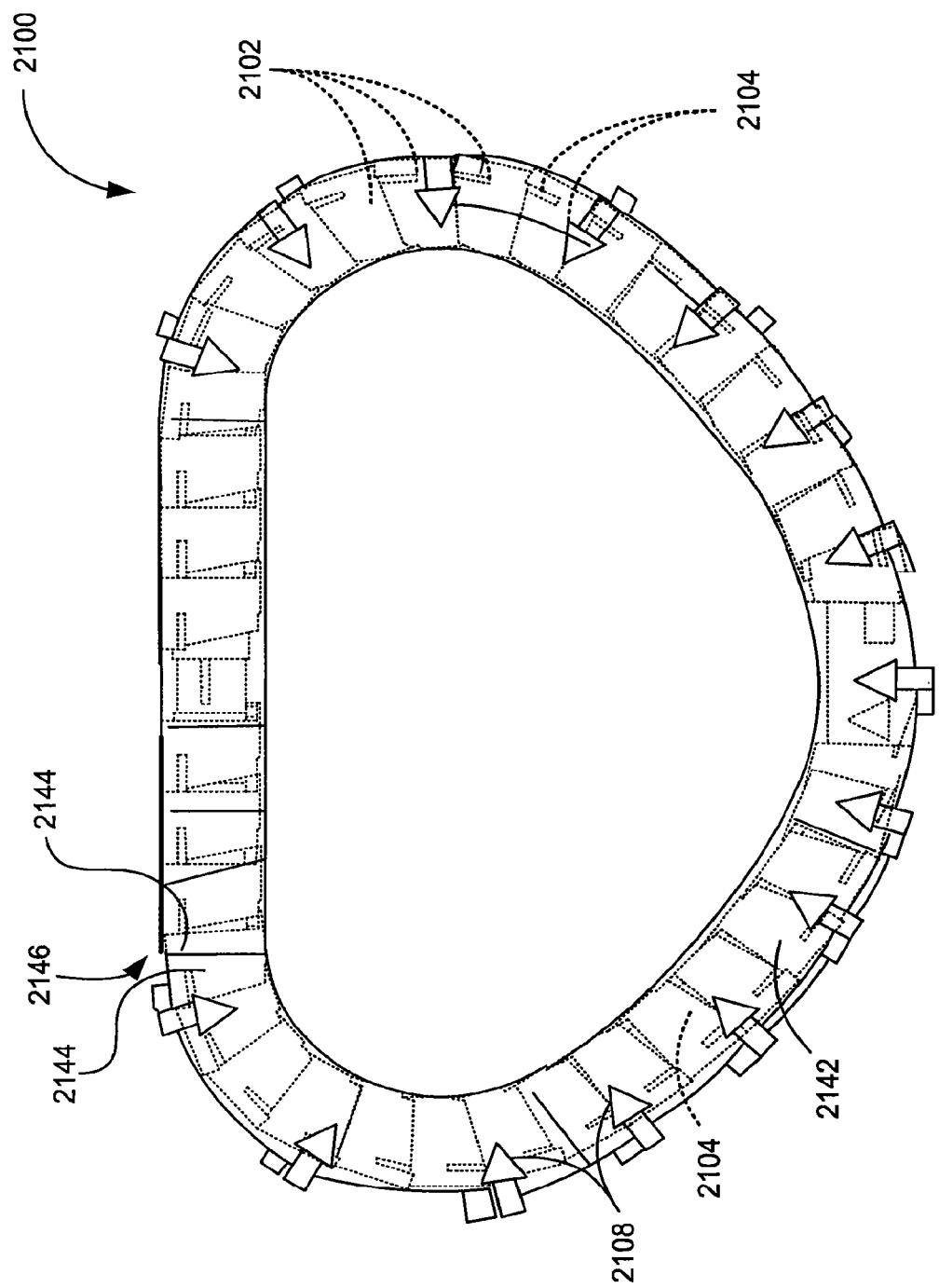
FIG. 21A is a schematic diagram illustrating a percutaneous transcatheter annuloplasty ring according to another embodiment.
Figure 21B:
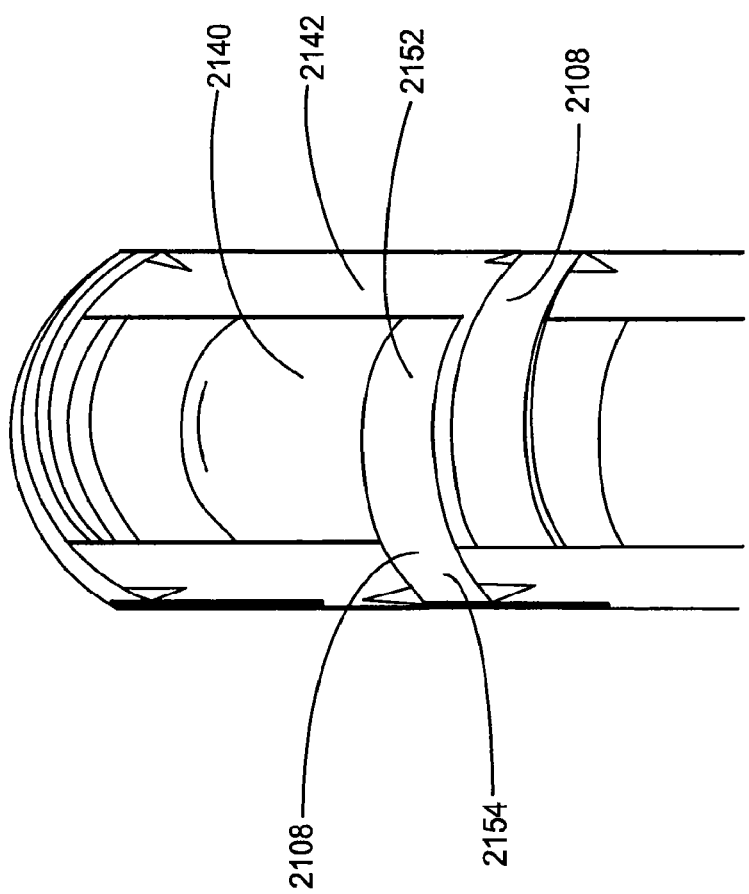
FIG. 21B is a schematic diagram illustrating an enlarged side view of the annuloplasty ring of FIG. 21A according to one embodiment.

FIG. 21A is a schematic diagram illustrating a percutaneous transcatheter annuloplasty ring 2100 according to another embodiment. The annuloplasty ring 2100 is shown in FIG. 21A in an annular operable geometry with anchors 2108 in an introduction configuration. FIG. 21B is a schematic diagram illustrating an enlarged side view of the annuloplasty 2100 ring of FIG. 21A. The annuloplasty ring 2100 may include an inner support structure 2140 and an outer shell 2142. In FIG. 21A, the inner support structure 2140 is shown in phantom lines as being hidden by the outer shell 2142. The inner support structure 2140 may be formed of a plurality of segments 2102, as shown in FIG. 1D and discussed more fully in other embodiments disclosed herein. The outer shell 2142 may be formed of a thin super-elastic material, such as Nitinol. The anchors 2108 may extend from and/or be integrated with the outer shell 2142. Superelastic shape memory material in the plurality of segments 2102 of the inner support structure 2140 and/or the outer shell 2142 enable the annuloplasty ring 2100 to transition between an insertion geometry and an operable geometry.

The anchors 2108, when in an introduction configuration, may be folded or wrapped to lie in close proximity to the outer shell 2142, as shown in FIG. 21B, so as to not protrude away from the surface of the annuloplasty ring 2100. The anchors 2108 may include a prong 2152 and a barb 2154 at an end of the prong. The barb 2154 may facilitate securement of the anchor 2108 in tissue.

Figure 21C:
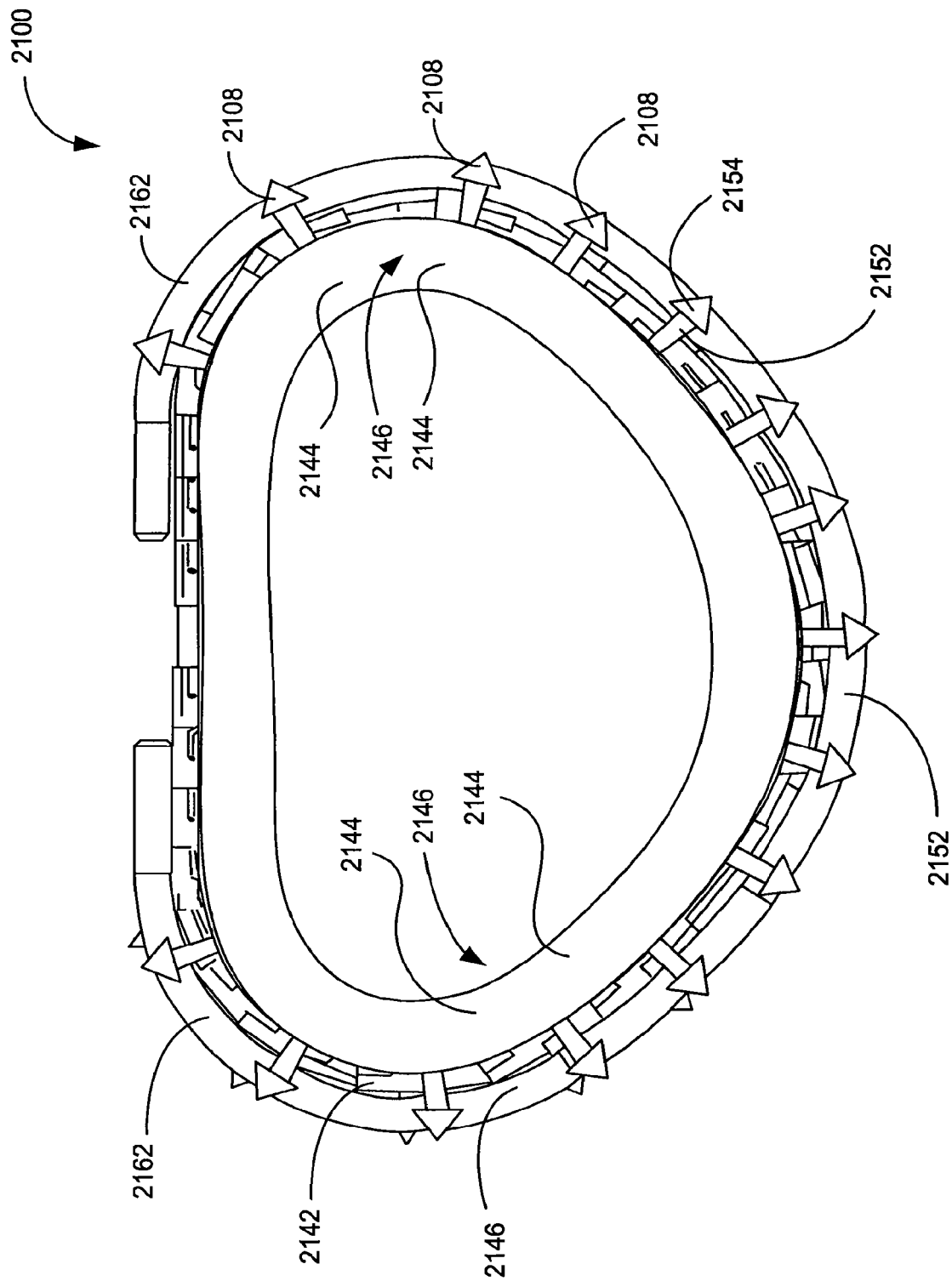
FIG. 21C is a schematic diagram of the annuloplasty ring of FIG. 21A with the anchors in an affixation configuration protruding away from the annuloplasty ring according to one embodiment.

FIG. 21C is a schematic diagram of the annuloplasty ring 2100 of FIG. 21A with the anchors 2108 in an affixation configuration protruding away from the annuloplasty ring 2100. An integrated diaphragm 2162 may be integrated with the outer shell 2142 and/or the inner support structure 2140. Inflation of the integrated diaphragm 2162 unfurls the anchors 2108 to expose the barbs 2154 for affixation (implantation) of the annuloplasty ring 2100 into a heart valve annulus. In another embodiment, rather than including an integrated diaphragm 2162, a balloon catheter (not shown) may be used to deploy the anchors 2108.

Those having skill in the art will understand from the disclosure herein that many changes may be made to the details of the above-described embodiments without departing from the underlying principles of the invention. The scope of the present invention should, therefore, be determined only by the following claims.

What is claimed is:

1. A system for percutaneous transcatheter delivery of an annuloplasty ring to repair a target valve of a heart via a trans-apical approach, the delivery apparatus comprising:
   a guide sheath having a lumen therethrough and configured to be positioned into an apex of a heart, the guide sheath having a length configured to be positioned through a ventricle of the heart, through the target valve, and into an atrium of the heart; and
   a balloon assembly configured to be within the guide sheath and advanced to a distal portion of the guide sheath, the balloon assembly comprising:
      the annuloplasty ring configured to be arranged in a compressed delivery geometry within a plane that is transverse to a longitudinal axis of the lumen of the guiding sheath, wherein the annuloplasty ring comprises a plurality of anchors configured to be pressed into and engage tissue of an annulus of the target valve, and free ends configured to be snapped together to decrease a diameter of the annuloplasty ring and thereby decrease a diameter of the annulus of the target valve, the annuloplasty ring further configured around a recess of the balloon assembly,
      an upper balloon portion adjacent a first side of the recess,
      a lower balloon portion adjacent a second side of the recess, and
      a double inflation lumen having an upper balloon inflation portion and a lower balloon inflation portion, the upper balloon inflation portion coupled to and configured to direct a fluid or gas into the upper balloon portion from outside the heart, the lower balloon inflation portion coupled to and configured to direct a fluid or gas into the lower balloon portion from outside the heart.

2. The system of claim 1, wherein:
the upper balloon portion is configured to inflate to restrict distal shifting of the annuloplasty ring relative to the recess as the delivery assembly is advanced and positioned in the target valve;
the lower balloon portion is configured to inflate to restrict proximal shifting of the annuloplasty ring relative to the recess as the delivery assembly is advanced and positioned in the target valve;
wherein the upper balloon portion and the lower balloon portion of the balloon assembly are more pliant than the recess of the balloon assembly to inflate and expand more readily than the recess, and wherein inflation of the balloon assembly to cause expansion of the recess expands the annuloplasty ring from the compressed delivery geometry to an expanded operable geometry.

3. The system of claim 1, wherein:
the upper balloon portion is configured to inflate to a diameter larger than the annulus of the target valve to restrict distal shifting of the annuloplasty ring and provide a surface that can be withdrawn to secure the annuloplasty ring against the annulus of the target valve; and
the lower balloon portion is configured to inflate to expand the annuloplasty ring from the compressed delivery geometry to an expanded operable geometry, wherein the annuloplasty ring in the compressed delivery geometry is disposed within the recess of the balloon assembly.

4. The system of claim 1, wherein the annuloplasty ring comprises shape memory material and a heating element to heat the shape memory material, the shape memory material configured to decreasing the diameter of the annuloplasty ring in response to heat provided by the heating element.

5. The system of claim 1, wherein the anchors of the annuloplasty ring are configured to be deployed by pulling one or more sutures coupled to the anchors, the one or more sutures extending through the guide sheath and out of an access site of the heart.

6. The system of claim 1, further comprising a knot pusher configured to knot a suture and push the suture from outside the heart to a point inside the heart adjacent the annuloplasty ring.

7. A system comprising:
a balloon assembly configured to be within a guide sheath and advanced to a distal portion of the guide sheath, the balloon assembly comprising:
an annuloplasty ring configured to be arranged in a delivery geometry, within a plane that is transverse to a longitudinal axis of a lumen of the guiding sheath, the annuloplasty ring comprising free ends configured to be snapped together to decrease a diameter of the annuloplasty ring and thereby decrease a diameter of an annulus of the a target valve,
an upper balloon portion adjacent a first side of a recess,
a lower balloon portion adjacent a second side of the recess, and
a double inflation lumen comprising an outer layer and an inner layer that combine to form a sealed passage, wherein the sealed passage is bisected to define an upper balloon inflation portion and a lower balloon inflation portion.

8. A system comprising:
a balloon assembly configured to be within a guide sheath and advanced to a distal portion of the guide sheath, the balloon assembly comprising:
an annuloplasty ring configured to be arranged in a delivery geometry, within a plane that is transverse to a longitudinal axis of a lumen and surrounds a recess of the balloon assembly, the annuloplasty ring comprising free ends configured to be snapped together to decrease a diameter of the annuloplasty ring and thereby decrease a diameter of an annulus of a target valve;
an upper balloon portion adjacent a first side of the recess,
a lower balloon portion adjacent a second side of the recess,
a double inflation lumen having an outer layer and an inner layer, the inner layer forming a shaft that runs through the center of the balloon assembly, and
a guide wire housed within the shaft.

* * * * *